US010982196B2

(12) United States Patent
Saint-Remy

(10) Patent No.: US 10,982,196 B2
(45) Date of Patent: *Apr. 20, 2021

(54) IMMUNOTHERAPY TARGETING INTRACELLULAR PATHOGENS

(71) Applicant: LIFE SCIENCES RESEARCH PARTNERS VZW, Leuven (BE)

(72) Inventor: Jean-Marie Saint-Remy, Grez-Doiceau (BE)

(73) Assignees: Life Sciences Research Partners VZW, Leuven (BE); Katholieke Universiteit Leuven, Leuven (BE)

( * ) Notice: Subject to any disclaimer, the term of this patent is extended or adjusted under 35 U.S.C. 154(b) by 827 days.

This patent is subject to a terminal disclaimer.

(21) Appl. No.: 14/450,722

(22) Filed: Aug. 4, 2014

(65) Prior Publication Data

US 2014/0377299 A1   Dec. 25, 2014

Related U.S. Application Data

(62) Division of application No. 12/735,742, filed as application No. PCT/EP2009/051808 on Feb. 16, 2009, now abandoned.

(60) Provisional application No. 61/035,890, filed on Mar. 12, 2008.

(30) Foreign Application Priority Data

Feb. 14, 2008  (EP) .................... 08447009

(51) Int. Cl.
| | |
|---|---|
| *C07K 14/005* | (2006.01) |
| *A61K 39/145* | (2006.01) |
| *A61K 39/21* | (2006.01) |
| *A61K 39/385* | (2006.01) |
| *C12N 9/02* | (2006.01) |
| *C07K 14/35* | (2006.01) |
| *C07K 14/445* | (2006.01) |
| *C12N 7/00* | (2006.01) |
| *A61K 39/00* | (2006.01) |

(52) U.S. Cl.
CPC .......... *C12N 9/0051* (2013.01); *A61K 39/145* (2013.01); *A61K 39/21* (2013.01); *A61K 39/385* (2013.01); *C07K 14/005* (2013.01); *C07K 14/35* (2013.01); *C07K 14/445* (2013.01); *C12N 7/00* (2013.01); *A61K 39/00* (2013.01); *A61K 2039/57* (2013.01); *A61K 2039/6031* (2013.01); *A61K 2039/64* (2013.01); *C07K 2319/00* (2013.01); *C12N 2710/10022* (2013.01); *C12N 2740/16022* (2013.01); *C12N 2740/16034* (2013.01); *C12N 2760/16022* (2013.01); *C12N 2760/16034* (2013.01); *C12Y 108/01009* (2013.01)

(58) Field of Classification Search
None
See application file for complete search history.

(56) References Cited

U.S. PATENT DOCUMENTS

| | | |
|---|---|---|
| 4,599,231 A | 7/1986 | Milich et al. |
| 4,886,782 A | 12/1989 | Good et al. |
| 5,433,948 A | 7/1995 | Thomas et al. |
| 5,552,142 A | 9/1996 | Thomas et al. |
| 5,589,175 A | 12/1996 | Vahlne et al. |
| 5,633,234 A | 5/1997 | August et al. |
| 5,770,202 A | 6/1998 | Thomas et al. |
| 5,773,002 A | 6/1998 | Thomas et al. |
| 5,863,528 A | 1/1999 | Hawley et al. |
| 6,399,383 B1 | 6/2002 | Apt et al. |
| 6,602,509 B1 | 8/2003 | Saint-Remy et al. |
| 6,656,471 B1 | 12/2003 | Sastry et al. |
| 6,759,046 B1 | 7/2004 | Gaudernack et al. |
| 7,157,089 B1 | 1/2007 | Mizzen et al. |
| 7,306,804 B2 | 12/2007 | Sastry et al. |
| 8,999,346 B2 | 4/2015 | Saint-Remy |
| 9,044,507 B2 | 6/2015 | Saint-Remy |
| 9,248,171 B2 | 2/2016 | Saint-Remy |
| 9,249,202 B2 | 2/2016 | Saint-Remy |
| 9,394,517 B2 | 7/2016 | Saint-Remy |
| 9,861,661 B2 * | 1/2018 | Saint-Remy ........... A61K 39/12 |
| 10,023,847 B2 | 7/2018 | Saint-Remy |
| 2003/0049723 A1 | 3/2003 | Zhang et al. |
| 2003/0104570 A1 | 6/2003 | Cabezon Silva et al. |
| 2003/0129205 A1 | 7/2003 | Saint-Remy et al. |
| 2003/0152581 A1 | 8/2003 | Saint-Remy et al. |
| 2004/0077045 A1 | 4/2004 | Zhang et al. |
| 2005/0032039 A1 | 2/2005 | Sastry et al. |
| 2005/0107256 A1 | 5/2005 | Barnwell et al. |
| 2005/0196386 A1 | 9/2005 | Blazar et al. |
| 2005/0202044 A1 | 9/2005 | Mizzen et al. |

(Continued)

FOREIGN PATENT DOCUMENTS

| | | |
|---|---|---|
| JP | 2004-147649 | 5/2004 |
| WO | WO-8504103 A1 | 9/1985 |
| WO | WO-9205800 A1 | 4/1992 |
| WO | WO 1993/08279 | 4/1993 |
| WO | WO-9405790 A1 | 3/1994 |

(Continued)

OTHER PUBLICATIONS

Freeman, W.H. (Molecular Cell Biology, 4th Edition, Lodish et al, Eds, New York, 2000, section 6.3).*

(Continued)

*Primary Examiner* — G. R. Ewoldt
*Assistant Examiner* — Marianne DiBrino
(74) *Attorney, Agent, or Firm* — Nixon & Vanderhye, PC

(57) ABSTRACT

The present invention relates to the use of immunogenic peptides comprising a T-cell epitope derived from an intracellular pathogen-associated antigen and a redox motif such as C-(X)2-[CST] or [CST]-(X)2-C in the prevention and/or treatment of infection with an intracellular pathogen and in the manufacture of medicaments therefore.

18 Claims, 1 Drawing Sheet

Specification includes a Sequence Listing.

(56) References Cited

U.S. PATENT DOCUMENTS

| | | |
|---|---|---|
| 2006/0182763 A1 | 8/2006 | Kim et al. |
| 2006/0211091 A1 | 9/2006 | Zhang et al. |
| 2006/0216301 A1 | 9/2006 | Tahara et al. |
| 2006/0269561 A1 | 11/2006 | Paterson et al. |
| 2007/0160620 A1 | 7/2007 | Mizzen et al. |
| 2007/0184023 A1 | 8/2007 | Rasmussen et al. |
| 2008/0176247 A1 | 7/2008 | Chou et al. |
| 2009/0012004 A1 | 1/2009 | Sette et al. |
| 2010/0068193 A1 | 3/2010 | Brunsvig et al. |
| 2010/0183652 A1 | 7/2010 | Page et al. |
| 2010/0203083 A1 | 8/2010 | Lux et al. |
| 2010/0303866 A1 | 12/2010 | Saint-Remy |
| 2010/0330088 A1 | 12/2010 | Saint-Remy |
| 2011/0002903 A1 | 1/2011 | Saint-Remy |
| 2011/0110964 A1 | 5/2011 | Saint-Remy |
| 2011/0111395 A1 | 5/2011 | Saint-Remy |
| 2011/0111502 A1 | 5/2011 | Saint-Remy |
| 2012/0009678 A1 | 1/2012 | Saint-Remy |
| 2013/0095133 A1 | 4/2013 | Klatzmann et al. |
| 2013/0259885 A1 | 10/2013 | Saint-Remy |
| 2014/0370044 A1 | 12/2014 | Saint-Remy |
| 2015/0110821 A1 | 4/2015 | Saint-Remy |
| 2015/0216901 A1 | 8/2015 | Saint-Remy |
| 2016/0091492 A1 | 3/2016 | Saint-Remy et al. |
| 2016/0108103 A1 | 4/2016 | Saint-Remy |
| 2016/0194367 A1 | 7/2016 | Saint-Remy |
| 2016/0250255 A1 | 9/2016 | Saint-Remy et al. |
| 2016/0339121 A1 | 11/2016 | Saint-Remy et al. |
| 2017/0100466 A1 | 4/2017 | Saint-Remy |
| 2018/0228912 A1 | 8/2018 | Saint-Remy et al. |
| 2018/0258154 A1 | 9/2018 | Saint-Remy et al. |
| 2018/0346887 A1 | 12/2018 | Saint-Remy |
| 2019/0106477 A1 | 4/2019 | Vander Elst |

FOREIGN PATENT DOCUMENTS

| | | |
|---|---|---|
| WO | WO-9740852 A1 | 11/1997 |
| WO | WO 1999/058552 | 11/1999 |
| WO | WO-0029008 A2 | 5/2000 |
| WO | WO 2001/070263 | 9/2001 |
| WO | WO 2002/000892 | 1/2002 |
| WO | WO 2002/095051 | 11/2002 |
| WO | WO 02/097070 A1 | 12/2002 |
| WO | WO-03072731 A2 | 9/2003 |
| WO | WO 2004/018667 | 3/2004 |
| WO | WO 2004/024766 | 3/2004 |
| WO | WO 05/012502 | 2/2005 |
| WO | WO 2005/039613 | 5/2005 |
| WO | WO-2005042575 A2 | 5/2005 |
| WO | WO 2005/086781 | 9/2005 |
| WO | WO 2006/059529 | 6/2006 |
| WO | WO 2007/104715 | 9/2007 |
| WO | WO-2007135684 A2 | 11/2007 |
| WO | WO 2008/017517 | 2/2008 |
| WO | WO-2009042215 A3 | 4/2009 |
| WO | WO 2009/100505 | 8/2009 |
| WO | WO 2009/101204 | 8/2009 |
| WO | WO 2009/101205 | 8/2009 |
| WO | WO 2009/101206 | 8/2009 |
| WO | WO 2009/101207 | 8/2009 |
| WO | WO 2009/101208 | 8/2009 |
| WO | WO-2009106073 A2 | 9/2009 |
| WO | WO-2010037395 A2 | 4/2010 |
| WO | WO-2012069568 A2 | 5/2012 |
| WO | WO-2013113076 A1 | 8/2013 |
| WO | WO-2013121296 A1 | 8/2013 |
| WO | WO-2015063176 A1 | 5/2015 |
| WO | WO-2016059236 A1 | 4/2016 |

OTHER PUBLICATIONS

Rancaniello, V. (2013).*
Tindle et al (PNAS, 1991, 88:5887-5891).*
Azoury-Ziadeh et al (Viral Immunology, 1999, 12(4): 297-312).*
MedlinePlus Medical Dictionary (Merriam Webster, Inc., 2017).*
Molecular Cell Biology (2000, W.H.Freeman and Company, 4th Ed.) (Year: 2000).*
Racaniello, V. (Virology Blog, 2013) (Year: 2013).*
ViralZone (2017) (Year: 2017).*
DermNet Nz (2019) (Year: 2019).*
HLA Nomenclature 2015 (Year: 2015).*
Parrino et al (Emerging Infection Diseases, 2007, 12(2): 191-198) (Year: 2007).*
Laforge et al (PLOS pathogens, 2011, 7(6): 1-16) (Year: 2011).*
Office Action dated Sep. 7, 2016, issued in connection with U.S. Appl. No. 14/686,855 (filed Apr. 15, 2015; Title: Elimination of Immune Responses to Viral Vectors; Applicants: Life Sciences Research Partners VZW and Katholieke Universiteit Leuven; Inventor: Saintremy).
Canadian Examination Report dated Oct. 19, 2015, issued in connection with Canadian Patent Application No. 2,715,611.
European Office Action dated Aug. 12, 2014, issued in connection with European Patent Application No. 09 711 066.2.
European Office Action dated Aug. 7, 2014, issued in connection with European Patent Application No. 13 151 000.0.
Examination Report dated Aug. 19, 2013, issued in connection with Australian Patent Application No. 2009214042.
Li Pira et al, "High throughput T epitope mapping and vaccine development" The Journal of Biomedicine and Technology, 2010, vol. 2010, 12 pages.
Crompton et al "Advances and challenges in malaria vaccine development" The Journal Clinical Investigation, 2010, vol. 120, pp. 4168-4178.
Sette et al, "Epitope-based vaccines: an update on epitope identification, Vaccine Design and Delivery", Current Opinion in Immunology, 2003, vol. 15, pp. 461-470.
Rope et al, "SARS Vaccines: Where are We?", Expert Review of Vaccines, 2009, vol. 8, pp. 887-898, Roper et al.
Hsu et al, "Assessing computational amino acid—turn propensities with a phage-displayed combinatorial library and directed evolution", Structure, 2006, vol. 14, pp. 1499-1510.
Written Description Training Materials, Mar. 25, 2008, U.S. Patent and Trademark Office (http://www.uspto.gov/web/menu/written.pdf).
Mach et al, "Regulation of MHC Class II—Genes: lessons from a Disease", Annu Rev Immunol, 1996, 14:301-331 specifically p. 302.
Thomson et al, "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: a Novel Approach to Vaccine Design", J. of Virol, 1998, 72(3):2246-2252.
Teuku et al, "The CXXC motif at the N terminus of an α-helical peptide", Protein Science, 2006, 15:1945-1950, Teuku Iqbalsyah et al.
Park et al, "Redox Regulation Facilitates Optimal Peptide Selection by MHC Class I during Antigen Processing", Cell, 2006, 127:369-382.
International Search Report for PCT/BE2008/000010, dated Jul. 2, 2008.
Written Opinion of the International Searching Authority for PCT/BE2008/000010, dated Jul. 2, 2008.
International Search Report for PCT/EP2009/051806, dated Aug. 11, 2009.
Written Opinion of the International Searching Authority for PCT/EP2009/051806, dated Aug. 11, 2009.
International Search Report for PCT/EP2009/051804, dated Aug. 11, 2009.
Written Opinion for PCT/EP2009/051804, dated Aug. 11, 2009.
International Search Report for PCT/EP2009/051803, dated Aug. 11, 2009.
Zhao et al, "Activated CD4+CD25+ T cells selectively kill B Lymphocytes", Blood, vol. 107, No. 10; pp. 3925-3932; May 15, 2006.
Aleksza, M. et al., "Altered cytokine expression of peripheral blood lymphocytes in polymyositis and dermatomyositis", Ann. Rheum. Dis., vol. 64, (2005), pp. 1485-1489.

(56) References Cited

OTHER PUBLICATIONS

Bolivar, J. et al, "Molecular cloning of a zinc finger autoantigen transiently associated with interphase nucleolus and mitotic centromeres and midbodies. Orthologous proteins with nine CXXC motifs highly conserved form nematodes to humans", J. Biol, Chem., vol. 274, (1999), pp. 36456-36464.
Braun, M.Y. et al., "Acute rejection in the absence of cognate recognition of allograft by T cells", J. Immunol., vol. 166, No. 8, (2001), pp. 4879-4883.
Brinster, C. et al., "Costimulatory effects of IL-1 on the expansion/differentiation of CD4+CD25+Foxp3+ and CD4+CD25+Foxp3− T cells", J. Leukoc. Biol., vol. 84, (2008), pp. 480-487.
Cao, O. et al, Prevention of gene transfer-induced inhibitor formation by nasal administration of human F.IX T cell epitope in a murine model of hemophilia B., Blood, vol. 104, (2004), pp. 121A-122A.
Chen, T. C. et al., "Induction of dominant transplantation tolerance by an altered peptide ligand of the male antigen Dby.", J Clin. Invest., vol. 113, No. 12, (2004), pp. 1754-1762.
Davids, B.J. et al., A new family of giardial cysteine-rich non-VSP protein genes and a novel cyst protein, PLOS. One., vol. 1, (2006), e44.
De La Cruz, V.F. et al., "The immunologic significance of variation within malaria circumsporozoite protein sequences", J. Immunol., vol. 142, (1989), pp. 3568-3575.
Eberl, G. et al., "Tissue-specific segregation of CD1d-dependent and CD1d-independent NK T cells", J. Immunol., vol. 162, (1999), pp. 6410-6419.
Dobrzynski, E. et al, "Prevention of cytotoxic T lymphocyte responses to factor IX-expressing hepatocytes by gene transfer-induced regulatory T cells", Proc. Natl. Acad Sci. U.S.A., vol. 103, (2006), pp. 4592-4597.
Fomenko, D.E. et al., "Identity and functions of CxxC-derived motifs", Biochemistry, vol. 42, (2003), pp. 11214-11225.
Geluk, A. et al., "HLA-DR binding analysis of peptides from islet antigens in IDDM", Diabetes, vol. 47, (1998), pp. 1594-1601.
Gross, D.A. et al., "Simple conditioning with monospecific CD4+CD25+ regulatory T cells for bone marrow engraftment and tolerance to multiple gene products", Blood, vol. 108, No. 6, (2006), pp. 1841-1848.
Grossman, W.J., et al., "Differential expression of granzymes A and B in human cytotoxic lymphocyte subsets and T regulatory cells", Blood, vol. 104, (2004), pp. 2840-2848.
Hohn, H. et al., "CD4+ tumor-infiltrating lymphocytes in cervical cancer recognize HLA-DR-restricted peptides provided by human papillomavirus-E7", J. Immunol., vol. 163, (1999), pp. 5715-5722.
Hori, S. et al., "Control of regulatory T cell development by the transcription factor Foxp3", Science, vol. 299, (2003), pp. 1057-1061.
Ise, W. et al., "Naïve CD4+ T cells exhibit distinct expression patterns in cytokines and cell surface molecules on their primary responses to varying doses of antigen", J. Immunol., vol. 168, (2002), pp. 3242-3250.
James, E. et al., HY peptides modulate transplantation responses to skin allografts, Int. Immunol., vol. 14, No. 11, (2002), pp. 1333-1342.
Joffre, O. et al., "Induction of antigen-specific tolerance to bone marrow allografts with CD4+CD25+ T lymphocytes", Blood, vol. 103, No. 11, (2004), pp. 4216-4221.
Louis, S. et al., "Contrasting CD25hiCD4+ T cells/FOXP3 patterns in chronic rejection and operational drug-free tolerance", Transplantation, vol. 81, (2006), pp. 398-407.
Maeda, M. et al., "CD1d-independent NKT cells in beta 2-microglobulin-deficient mice have hybrid phenotype and function of NK and T cells", J. Immunol., vol. 172, (2004), pp. 6115-6122.
Maynard, C.L. et al., "Regulatory T cells expressing interleukin 10 develop from Foxp3+ and Foxp3− precursor cells in the absence of interleukin 10", Nat. Immunol., vol. 8, (2007), pp. 931-941.

Qin, W. et al., "Fusion protein of CDR mimetic peptide with Fc inhibit TNF-alpha induced cytotoxicity", Mol. Immunol., vol. 43, (2006), pp. 660-666.
Roopenian, D. et al., "The immunogenomics of minor histocompatibility antigens", Immunol. Rev., vol. 190, (2002), pp. 86-94.
Saez-Borderias, A. et al, "Expression and function of NKG2D in CD4+ T cells specific for human cytomegalovirus", Eur. J. Immunol., vol. 36, (2006), pp. 3198-3206.
Stenstrom, M. et al., "Natural killer T-cell populations in C57BL/6 and NK1.1 congenic BALB.NK mice—a novel thymic subset defined by BALB.NK mice", Immunology, vol. 114, (2005), pp. 336-345.
Sundar, S.K. et al., "Generation of Epstein-Bar virus antigen-specific suppressor T cells in vitro", Int. J. Cancer, vol. 35, (1985), pp. 351-357.
Taylor, A. et al., "T regulatory cells and allergy", Microbes and Infection, vol. 7, (2005), pp. 1049-1055.
Tsuji, N.M. et al, "Antigen-specific, CD4+CD25+ regulatory T cell clones induced in Peyer's patches", Int. Immunol., vol. 15, (2003),pp. 525-534.
Voo, K.S. et al., "Functional characterization of EBV-encoded nuclear antigen 1-specific CD4+ helper and regulatory T cells elicited by in vitro peptide stimulation", Cancer Res., vol. 65, (2005), pp. 1577-1586.
Wang, R.F., "Immune suppression by tumor-specific CD4+ regulatory T-cells in cancer", Semin. Cancer Biol., vol. 16, (2006), pp. 73-79.
Wiker, H.G. et al., "Cloning, expression and significance of MPT53 for identification of secreted proteins of *Mycobacterium tuberculosis*", Microb. Pathog., vol. 26, (1999), pp. 207-219.
Wood, K.J. et al., "Regulatory T cells in Transplantation tolerance", Nat. Rev. Immunol., vol. 3, (2003), pp. 199-210.
Haveman, L.M. et al., Induction and capture of CD4+ cytotoxic adenoviral specific T-cells in response to pan-DR binding adenoviral epitopes toward immunotherapy, Blood, vol. 106, (2005), Abstract 3238.
Arunalacham et al, Enzymatic reduction of disulfide bonds in lysosomes: Characterization of a Gamma-interferon-inducible lysosomal thiol reductase (GILT), (2000) Proc. Natl. Acad. Sci USA, vol. 97, No. 2, 745-750.
Bower et al "Two Members of the Thioredoxin-h Family Interact with the Kinase Domain of a *Brassica* S Locus Receptor Kinase", (1996) The plant cell, vol. 8, 1641-1650.
Brinks et al, "Immunogenicity of Therapeutic Proteins: The Use of Animal Models", (2011) Phar res 28,2379-2385.
Capon et al, "The CD4-gp120 Interaction and Aids Pathogenesis" (1991) Ann. Rev. Immunol 9, 649-678.
Carlier et al, "Increased Synapse Formation Obtained by T Cell Epitopes Containing a CxxC Motif in Flanking Residues Convert CD4+ T Cells into Cytolytic Effectors", 2012 PlosOne vol. 7, Issue 10, e45366.
Chen et al, "Glucocorticoid amplifies IL-2-dependent expansion of functional FoxP3+CD4+CD25+ T regulatory cells in vivo and enhances their capacity to suppress EAE", (2006) Eur. J. Immunol. 36, 2139-2149.
Corthay et a "CD4+ T Cells Cooperate with Macrophages for Specific Elimination of MHC Class II-Negative Cancer Cells", (2007) Adv Exp Med Biol. 590, 195-208.
Dobrzanski, "Expanding roles for CD4T cells and their subpopulations in tumor immunity and therapy", (2013) Front. Oncology, vol. 3, Article 63, 1-19.
Fan et al, "Co-immunization of BALB/c mice with recombinant immunogens containing G protein fragment and chimeric CTL epitope of respiratory syncytial virus induces enhanced cellular immunity and high level of antibody response", (2005) Vaccine 23, 4453-4461.
Ge et al, "An hsp 70 fusion protein vaccine potentiates the immune response against Japanese encephalitis virus", (2007) Arch. Viral 152, 125-135.
Gentile et al, "Thyroglobulin as an autoantigen: what can we learn about immunopathogenicity from the correlation of antigenic properties with protein structure?", (2004) Immunol 112 13-25.

(56) References Cited

OTHER PUBLICATIONS

Hague, "Cysteinylation of MHC Class II Ligands: Peptide Endocytosis and Reduction Within APC Influences T Cell Recognition[1]", (2001) J. Immunol. 166, 4543-4551.
Harris, Prediction of murine MHC class I epitopes in a major house dust mite allergen and induction of T1-type CD8+ T cell responses, (1997) Int. Immunol., vol. 9, No. 2, 273-280.
Janssens et al, "CD4+ CD25+ T Cells Lyse Antigen-Presenting B Cells by Fas-Fas Ligand Interaction in an Epitope-Specific Manners", (2003) J. Immunol. 171, 4604-4612.
Jensen, "Acidification and Disulfide Reduction Can be Sufficient to Allow Intact Proteins to Bind Class II MHC[1]", (1993) J. Immunol. 150, No. 8, 3347-3356.
Wobus et al, "Embryonic Stem Cells: Prospects for Developmental Biology and Cell Therapy", (2005) Physiol Rev 85: 635-678.
Khare et al, "HLA class II transgenic mice authenticate restriction of myelin oligodendrocyte glycoprotein-specific immune response implicated in multiple sclerosis pathogenesis", (2003) Int. Immunol. 15, No. 4, 535-546.
Maekawa et al, "Evidence for a Domain-Swapped CD4 Dimer as the Coreceptor for Binding to Class II MHC[1]", (2006) J. Immunol. 176(11), 6873-6878.
Matthias et al, "Disulfide exchange in domain 2 of CD4 is required for entry of HIV-1", (2002) Nature immunol 3, No. 8, 727-732.
Okubo et al, "Analysis of HLA-DRB1*0901-binding HPV-16 E7 helper T cell epitope[1]", (2004) J Obstet Gynaecol Res. 30(2), 120-129.
Oliviera et al, "Insights into the Specificity of Thioredoxin Reductase-Thioredoxin Interactions. A Structural and Functional Investigation of the Yeast Thioredoxin System", (2010) biochemistry 49, 3317-3326.
Park et al, "Redox Regulation Facilitates Optimal Peptide Selection by MHC Class I during Antigen Processing", (2006) cell 127, 369-372.
Roep et al, "The problems and promises of research into human immunology and autoimmune disease", (2012) Nature Med 18(1) 48-53.
Santin et al, "Human Papillomavirus Type 16 and 18 E7-Pulsed Dendritic Cell Vaccination of Stage IB or IIA Cervical Cancer Patients: a Phase I Escalating-Dose Trial", (2008) J. Virol. 82, No. 4, 1968-1979.
Savoldo et al, "Generation of EBV-Specific CD4+ Cytotoxic T Cells from Virus Naive Individuals[1]", (2002) J Immunol. 168(2), 909-918.
Shi et al, "A novel plasma membrane-bound thioredoxin from soybean", (1996) Plant Mol. Biol. 32, 653-662.
Texier et al, "On the diversity and heterogeneity of $H-2^d$-restricted determinants and T cell epitopes from the major bee venom allergen", (1999) Int Immunol. 11, 1313-1325.
Tindle et al, "A "public" T-helper epitope of the E7 transforming protein of human papillomavirus 16 provides cognate help for several E7 B-cell epitopes from cervical cancer-associated human papillomavirus genotypes", (1991) Proc Natl. Acad. Sci 88, 5887-5891.
Weissert et al, "MHC Class II-Regulated Central Nervous System Autoaggression and T Cell Responses in Peripheral Lymphoid Tissues Are Dissociated in Myelin Oligodendrocyte Glycoprotein-Induced Experimental Autoimmune Encephalomyelitis[1]", (2001) J. Immunol. 166, 7588-7599.
Wekerle et al, "Autoimmunity's next top models", (2012) Nature Med. 18(1), 66-70.
Wu et al, "Engineering an intracellular pathway for major histocompatibility complex class II presentation of antigens", (1995) Proc. Natl. Acad. Sci. 92, 11671-11675.
Toyokawa et al, "Relative Contribution of Direct and Indirect Allorecognition in Developing Tolerance After Liver Transplantation", 2008 Liver Transpl. 14(3) 346-357.
Boisgerault et al, "Differential roles of direct and indirect allorecognition pathways in the rejection of skin and corneal transplants", (2009) Transplantation 87(1): 16-23.

Li et al, "Twisting immune responses for allogeneic stem cell therapy", (2009) World J Stem Cells 1(1), 30-35.
Batten et al, "Immune response to stem cells and strategies to induce tolerance", (2007) Phil. Trans. R. Soc. B 362, 1343-1356.
Heemskerk (2006) J. Immunol. 177, 8851-8859 "Adenovirus-Specific CD4 T Cell Clones Recognizing Endogenous Antigen Inhibit Viral Replication In Vitro through Cognate Interaction".
European Examination Report dated Mar. 6, 2015, issued in connection with European Patent Application No. 13 187 209.5.
EP Examination Report dated Apr. 26, 2013, issued in connection with European Patent Application No. 09 711 066.2.
European Search Report dated Jul. 9, 2013, issued in related European Patent Application No. 13150811.1.
European Search Report dated Jul. 9, 2013, issued in corresponding European Patent Application No. 13151000.0.
Moldovan et al, "CD4 Dimers Constitute the Functional Component Required for T Cell Activation", The Journal of Immunology 2002, 169:6261-6268.
Canadian Examination Report dated Feb. 26, 2015, issued in connection with Canadian Patent Application No. 2,715,484.
Examination Report dated Apr. 20, 2016, issued in connection with Canadian Patent Application No. 2,715,484 (Title: Elimination of Immune Responses to Viral Vectors; Applicants: Life Sciences Research Partners VZW and Katholieke Universiteit Leuven; Inventor: Saintremy).
Office Action dated Dec. 1, 2017 in U.S. Appl. No. 14/980,932, filed Dec. 28, 2015, related application.
Office Action dated Sep. 11, 2018 in U.S. Appl. No. 14/980,932, filed Dec. 28, 2015, related application.
Final Office Action dated Jan. 8, 2019 in U.S. Appl. No. 14/980,932, filed Dec. 28, 2015, related application.
Notice of Allowance dated Apr. 3, 2019 in U.S. Appl. No. 14/980,932, filed Dec. 28, 2015, related application.
Office Action dated Oct. 2, 2018 in U.S. Appl. No. 15/388,398, filed Dec. 22, 2016, related application.
Final Office Action dated Apr. 15, 2019 in U.S. Appl. No. 15/388,398, filed Dec. 22, 2016, related application.
Office Action dated Aug. 17, 2016 in U.S. Appl. No. 14/589,134, filed Jan. 5, 2015, related application.
Final Office Action dated Dec. 2, 2016 in U.S. Appl. No. 14/589,134, filed Jan. 5, 2015, related application.
Advisory Action dated Mar. 20, 2017 in U.S. Appl. No. 14/589,134, filed Jan. 5, 2015, related application.
Office Action dated Jul. 14, 2017 in U.S. Appl. No. 14/589,134, filed Jan. 5, 2015, related application.
Final Office Action dated Jan. 19, 2018 in U.S. Appl. No. 14/589,134, filed Jan. 5, 2015, related application.
Office Action dated Oct. 5, 2018 in U.S. Appl. No. 14/589,134, filed Jan. 5, 2015, related application.
Notice of Allowance dated Feb. 21, 2019 in U.S. Appl. No. 14/589,134, filed Jan. 5, 2015, related application.
Office Action dated Sep. 7, 2018 in U.S. Appl. No. 14/894,221, 371(c) date Nov. 25, 2015, related application.
Notice of Allowance dated Apr. 15, 2019 in U.S. Appl. No. 14/894,221, 371(c) date Nov. 25, 2015, related application.
Office Action dated Jun. 8, 2018 in U.S. Appl. No. 15/151,868, filed May 11, 2016, related application.
Final Office Action dated Mar. 19, 2019 in U.S. Appl. No. 15/151,868, filed May 11, 2016, related application.
Office Action dated Feb. 23, 2017 in U.S. Appl. No. 14/375,324, 371(c) dated Jul. 29, 2014, related application.
Final Office Action dated Oct. 30, 2017 in U.S. Appl. No. 14/375,324, 371(c) dated Jul. 29, 2014, related application.
Office Action dated Jun. 25, 2018 in U.S. Appl. No. 14/375,324, 371(c) dated Jul. 29, 2014, related application.
Final Office Action dated Mar. 25, 2019 in U.S. Appl. No. 14/375,324, 371(c) dated Jul. 29, 2014, related application.
Office Action dated Feb. 20, 2018 in U.S. Appl. No. 14/976,259, filed Dec. 21, 2015, related application.
Final Office Action dated Oct. 26, 2018 in U.S. Appl. No. 14/976,259, filed Dec. 21, 2015, related application.
Advisory Action dated Feb. 4, 2019 in U.S. Appl. No. 14/976,259, filed Dec. 21, 2015, related application.

(56) References Cited

OTHER PUBLICATIONS

Office Action dated May 17, 2019 in U.S. Appl. No. 14/976,259, filed Dec. 21, 2015, related application.
Office Action dated Sep. 18, 2018 in U.S. Appl. No. 15/516,045, 371(c) date Mar. 31, 2017, related application.
Final Office Action dated Feb. 13, 2019 in U.S. Appl. No. 15/516,045, 371(c) date Mar. 31, 2017, related application.
Office Action dated Jan. 20, 2012 in U.S. Appl. No. 12/377,048, 371(c) date Feb. 20, 2009, related application.
Final Office Action dated Aug. 9, 2012 in U.S. Appl. No. 12/377,048, 371(c) date Feb. 20, 2009, related application.
Office Action dated Apr. 20, 2015 in U.S. Appl. No. 12/377,048, 371(c) date Feb. 20, 2009, related application.
Notice of Allowance dated Sep. 22, 2015 in U.S. Appl. No. 12/377,048, 371(c) date Feb. 20, 2009, related application.
Office Action dated Jan. 9, 2014 in U.S. Appl. No. 12/735,744, 371(c) date Aug. 13, 2010, related application.
Final Office Action dated May 20, 2014 in U.S. Appl. No. 12/735,744, 371(c) date Aug. 13, 2010, related application.
Office Action dated Nov. 25, 2014 in U.S. Appl. No. 12/735,744, 371(c) date Aug. 13, 2010, related application.
Final Office Action dated Jun. 5, 2015 in U.S. Appl. No. 12/735,744, 371(c) date Aug. 13, 2010, related application.
Notice of Allowance dated Sep. 28, 2015 in U.S. Appl. No. 12/735,744, 371(c) date Aug. 13, 2010, related application.
Office Action dated Jul. 11, 2013 in U.S. Appl. No. 12/735,739, 371(c) date Aug. 13, 2010, related application.
Final Office Action dated Feb. 20, 2014 in U.S. Appl. No. 12/735,739, 371(c) date Aug. 13, 2010, related application.
Office Action dated Jan. 11, 2016 in U.S. Appl. No. 12/735,739, 371(c) date Aug. 13, 2010, related application.
Final Office Action dated Aug. 11, 2016 in U.S. Appl. No. 12/735,739, 371(c) date Aug. 13, 2010, related application.
Office Action dated Jan. 22, 2013 in U.S. Appl. No. 12/735,740, 371(c) date Aug. 13, 2010, related application.
Final Office Action dated Jul. 10, 2013 in U.S. Appl. No. 12/735,740, 371(c) date Aug. 13, 2010, related application.
Office Action dated Apr. 1, 2014 in U.S. Appl. No. 12/735,740, 371(c) date Aug. 13, 2010, related application.
Notice of Allowance dated Oct. 2, 2014 in U.S. Appl. No. 12/735,740, 371(c) date Aug. 13, 2010, related application.
Notice of Allowance dated Mar. 3, 2015 in U.S. Appl. No. 12/735,740, 371(c) date Aug. 13, 2010, related application.
Office Action dated Jan. 1, 2013 in U.S. Appl. No. 12/735,742, 371(c) date Aug. 13, 2010, related application.
Office Action dated Jun. 17, 2016 in U.S. Appl. No. 13/988,925, 371(c) date Jun. 6, 2013, related application.
Final Office Action dated Dec. 26, 2016 in U.S. Appl. No. 13/988,925, 371(c) date Jun. 6, 2013, related application.
Office Action dated Nov. 9, 2017 in U.S. Appl. No. 13/988,925, 371(c) date Jun. 6, 2013, related application.
Notice of Allowance dated Mar. 26, 2018 in U.S. Appl. No. 13/988,925, 371(c) date Jun. 6, 2013, related application.
Abrahimians et al., "MHC class II-restricted epitopes containing an oxidoreductase activity prompt CD4+ T cells with apoptosis-inducing properties," Frontiers in Immunology, 6(2), pp. 1-5 (2015).
Abrahimians, E. M., et al., "Thioreductase-Containing Epitopes Inhibit the Development of Type 1 Diabetes in the NOD Mouse Model," Frontiers in Immunology, 7(67), 10 pages (2016).
Aley & Gillin, "Giardia lambiia: post-translational processing and status of exposed cysteine residues in TSA 417, a variable surface antigen," Exp Parasitol, 77:295-305 (1993).
Apostolou et al., "Evidence for two subgroups of CD4–CD8– NKT cells with distinct TCR alpha beta repertoires and differential distribution in lymphoid tissues," J Immunol, 165(5):2481-2490 (2000).
Appella et al., "Analysis of the structure of naturally processed peptides bound by class I and class II major histocompatibility complex molecules," EXS, 73:105-119 (1995).

Ascherio et al., "Environmental factors in multiple sclerosis," Expert Rev Neurother, 13(12 S):3-9 (2013).
Azoury-Ziadeh et al., "T-Helper Epitopes Identified Within the E6 Transforming Protein of Cervical Cancer-Associated Human Papillomavirus Type 16," Viral Immunology, 12(4):297-312 (1999).
Balato et al., "Natural killer T cells: An unconventional T-cell subset with diverse effector and regulatory functions," Journal of Investigative Dermatology, 129:1628-1642 (2009).
Brinster et al., "Bone Marrow-Derived Dendritic Cells Reverse the Anergic State of CD4+CD25+ T Cells without Reversing Their Suppressive Function," The Journal of Immunology, 175:7332-7340 (2005).
Caro-Aguilar et al., "Chimeric epitopes delivered by polymeric synthetic linear peptides induce I protective immunity to malaria," Microbes Infect, 7:1324-1337 (2005).
Carlier et al., "Control of asthma by in vitro-induced allergen-specific regulatory T cells in the mouse," Munksgaard Allergy, 62(Suppl 83):555 (Abstract 1 616) (2007).
Castano et al., "Peptide binding and presentation by mouse CD1," Science, 269:223-226 (1995).
Cavone et al., "Long-term suppression of EAE relapses by pharmacological impairment of epitope spreading," Br J Pharmacol, 171(6):1501-1509 (2014).
Celts et al., "Induction of anti-tumor cytotoxic T lymphocytes in normal humans using primary cultures and synthetic peptide epitopes," Proc Natl Acad Sci USA, 91(6):2105-2109 (1994).
"Chapter III Immune Molecules," cited in Office Action in related Chinese Patent Application No. 201180056725.7, 9 pages.
Chuanlin ed., Molecular Immunology, Fudan University Press, Shanghai Medical College Press; publication date: May 2001; pp. 428-429, 433-436 (English language translation provided) (15 pages).
Cotton et al., "Oxidative inhibition of human soluble catechol-O-methyltransferase," Biol Chem, 279:23710-23718 (2004).
Crellin et al., "Altered activation of AKT is required for the suppressive function of human CD4+CD25+ T regulatory cells," Blood, 1 09(5):2014-2022 (2007).
Database Geneseq (online), "Human preproinsulin (PPI) antigenic peptide, SEQ ID 164," XP002770300, Jan. 26, 2017, retrieved from EBI accession No. GSP:BDK51134, Database accession No. BDK51134 sequence.
Davis et al., "Interrogating the repertoire: broadening the scope of peptide-MHC multimer analysis," Nature Rev Immunology,11:551-558 (2011).
De Groot et al., "Immunogenicity of Protein Therapeutics", Trends in Immunology, 28(11):482-490 (2007).
Desmetz et al., "Proteomics-Based Identification of HSP60 as a Tumor-Associated Antigen in Early Stage Breast Cancer and Ductal Carcinoma in situ," Journal of Proteome Research (2008), 7, 3830-3837.
Facktor et al., "Hypersensitivity to tetanus toxoid," J Allergy Clin Immunol, 52(1):1-12 (1973).
Francois et al., "The CD4+ T-Cell Response of Melanoma Patients to a MAGE-A3 Peptide Vaccine Involves Potential Regulatory T Cells," Cancer Res, 69(10):4335-4345 (2009).
Frankel et al., "Characterization of diphtheria fusion proteins targeted to the human interleukin-3 receptor," Protein Eng, 13(8):575-81 (2000).
Lodish et al., Molecular Cell Biology, 4th Edition, section 6.3, "Viruses: Structure, Function, and Uses," (2000).
GenBank AA5961 0.1, 1995, p. 1.
GenBank AAA58655.1, 1994, p. 1.
GenBank FPAA051928, 1997, p. 1.
GenBank M77349.1—Skonier et al., "Human transforming growth factor-beta induced gene product (BIGH3) mRNA, complete cds," Jan. 14, 1995, (3 pages).
GenPept PDB SGSB_A, 2017, pp. 1-2.
Girardi et al., "Structure of an alpha-helical peptide and lipopeptide bound to the nonclassical major histocompatibility complex (MHC) class I molecule CD1 d," J Biol Chem, 291(20):10677-10683 (2016).
Haveman et al., "Novel pan-DR-binding T cell epitopes of adenovirus induce pro-inflammatory cytokines and chemokines in healthy donors," Int Immunol, 18(11):1521-1529 (2006).

(56) References Cited

OTHER PUBLICATIONS

Hemmer, B., et al., "Minimal peptide length requirements for CD4+ T cell clones—implications for molecular mimicry and T cell survival," International Immunology, 12(3):375-383 (2000).
Ho et al., "CD4(−)CD8alphaalpha subset of CD1d-restricted NKT cells controls T cell expansion," J Immunol,172(12):7350-7358 (2004).
Iqbalsyah et al., "The CXXC motif at the N terminus of an .alpha.-helical peptide," Protein Sci, 15:1945-1950 (2006).
Janeway et al., Immunobiology, 3rd edition, Garland Press Inc., p. G:11 (1997).
Jiang et al., "Protection by the Gross Saponins of *Tribulus terrestris* Against Cerebral Ischemic Injury in Rats Involves the NF-KB Pathway," Acta Pharmaceutica Sinica B, 1(1):21-26 (2011).
Karin et al., "Reversal of Experimental Autoimmune Encephalomyelitis by a Soluble Peptide Variant of a Myelin Basic Protein Epitope: T Cell Receptor Antagonism and Reduction of Interferon γ and Tumor Necrosis Factor α Production," J Exp Med, 180(6):2227-2237 (1994).
Kasprowicz et al., "Tracking of Peptide-Specific CD4+ T-Cell Responses After and Acute Resolving Viral Infection: a Study of Parovirus 819," Journal of Virology, 80(22):11209-11217 (2006).
Klebanoff et al., "Therapeutic cancer vaccines: are we there yet?" Immunol Rev, 239:27-44 (2011).
Kumar, K. V. S. H. and Modi, K. D., "Twins and endocrinology," Indian J Endocrinol Metab, 18(Suppl 1):S48-5 (2014) 2. doi: 10.4103/2230-8210.145074.
Lewin et al., "Effects of substitutions in the CXXC active-site motif of the extracytoplasmic hioredoxin ResA," Biochem J, 414:81-91 (2008).
Lindqvist et al., "Both CD4+ FoxP3+ and CD4+ FoxP3− T cells from patients with B-cell malignancy express cytolytic markers and kill autologous leukaemic B cells in vitro," Immunology, 133:296-306 (2011).
Lovitch, S. B., et al., "Amino-Terminal Flanking Residues Determine the Conformation of a Peptide—Class II MHC Complex," The Journal of Immunology, 176:2958-2968 (2006).
Markovic-Plese et al., "T cell recognition of immunodominant and cryptic proteolipid protein epitopes in humans," J Immunol, 155(2):982-992 (1995) (12 pages).
Marti et al., "Conformationally Correct Expression of Membrane-Anchored Toxoplasma gondii SAG1 in the Primitive Protozoan Giardia duodenalis," Infection and Immunity, 70(2):1014-1016 (2002).
Massilamany et al., "Detection of autoreactive CD4 T cells using major histocompatibility complex class II dextramers," BMC Immunology, 12:40 (2011).
Matsuda et al., "CD1 d-reslricted iNKT cells, the 'Swiss-Army Knife' of the immune system," Current Opinion in Immunology, 20(3):358-368 (2008).
Merkler et al., "Myelin oligodendrocyte glycoprotein-induced experimental autoimmune encephalomyelitis in the common marmoset reflects the immunopathology of pattern II multiple sclerosis lesions," Multiple Sclerosis, 12:369-374 (2006).
Nepom, "MHC class II tetramers," The Journal of Immunology, 188:2477-2482 (2012).
Nielsen et al., "Quantitative Predictions of Peptide Binding to Any HLA-DR Molecule of Known Sequence: NetMHCIIpan," PLOS Comp Biol, 4(7):e1000107 (2008).
Ochoa-Garay et al., "The Ability of Peptides to Induce Cytotoxic T Cells In Vivo Does Not Strongly Correlate With Their Affinity for the H-2L$^d$ Molecule: Implications for Vaccine Design and Immunotherapy," Mol Immunol, 34(3):273-281 (1997).

Papanastasiou et al. "Primary structure and biochemical properties of a variant-specific surface protein of Giardia," Molecular and Biochemical Parasitology, 86:13-27 (1997).
Peterson, "Regulatory T-cells, diverse phenotypes integral to immune homeostasis and suppression," Toxic Path, 40(2):186-204 (2012).
Pillai et al., "Host NKT Cells Can Prevent Graft-versus-Host Disease and Permit Graft Antitumor Activity after Bone Marrow Transplantation," The Journal of Immunology, 178:6242-6251 (2007).
Printout from NetM HCIIpan Server—prediction results dated Sep. 26, 2018, 1 page.
Quintana et al., "Epitope spreading as an early pathogenic event in pediatric rnultiple sclerosis," Neurology, 83(24):2219-26 (2014).
Rammensee et al., "MHC Ligands and Peptide Motifs," Springer, New York & Austin, Texas, USA, p. 317 (1997).
Rancaniello, "How many viruses on earth?" Virology Blog (2013), virology.ws/2013/09/06/how-many-viruses-on-earth/.
Reznik et al., "Indirect Allorecognition of Mismatched Donor HLA Class II Peptides in Lung Transplant Recipients with Bronchiolitis Obliterans Syndrome," Am J Transpl, 1:228-235 (2001).
Robinson, Vaccine Protocols (Humana Press, 2003, Totowa, NJ, Ed. Andrew Robinson, Michael J. Hudson and Martin P. Cranage, pp. 121-123).
Schrieber et al., "Tumor immunogenicity and responsiveness to cancer vaccine therapy: The state of the art," Seminar. Immunol. 22:105-112 (2010).
Schultz et al., "A Mage-A3 Peptide Presented by HLA-DP4 Is Recognized on Tumor Cells by CD4+ Cytolytic T Lymphocytes1," Cancer Research, 60:6272-6275 (2000).
Schwartz et al., "The T lymphocyte response to cytochrome c. V. Determination of the minimal peptide size required for stimulation of T cell clones and assessment of the contribution of each residue beyond this size to antigenic potency," J Immunol, 135(4):2598-608 (1985).
Sette et al., "HLA supertypes and supermotifs: a functional perspective on HLA polymorphism," Curr Opinion Immunol, 10:478-482 (1998).
Straub et al., "Allelic variation in GAD1 (GAD67) is associated with schizophrenia and influences cortical function and gene expression," Molecular Psychiatry, 12:854-869 (2007).
Sundar et al., "Generation of Epstein-Bar virus antigen-specific suppressor T cells in vitro," Int J Cancer, 35:351-357 (1985).
Tisch et al., "Antigen-specific immunotherapy: Is it a real possibility to combat T-cell-mediated autoimmunity?" PNAS, 91:437-438 (1994).
UniProt P01906.2, 2017, p. 1-6.
UniProt O15523.2, 2017, pp. 1-7.
Vignali, D. A. A. and Strominger, J. L., "Amino Acid Residues that Flank Core Peptide Epitopes and the Extracellular Domains of CD4 Modulate Differential Signaling through the T Cell Receptor," J Exp Med, 179:1945-1956 (1994).
Wang et al., "Generation and characterization of HLA-A*2.1 restricted and Prostein 31-39 specific NKT cell lines," Acta Academiae Medicine Militaris Tertiae, 28(16):1652-1655 (2006) (English language translation provided) (11 pages).
Wooldridge et al., "Tricks with tetramers: how to get the most from multimeric peptide-MHC," Immunology, 126(2):147-164 (2009).
Zeng at al., "Crystal structure of mouse CD1: An MHC-like fold with a large hydrophobic binding groove," Science, 277:339-345 (1997).
Zhang et al., "A MAGE-3 Peptide Presented by HLA-DR1 to CD4+ T Cells That Were Isolated from a Melanoma Patient Vaccinated with a MAGE-3 Protein," J Immunol, 171:219-225 (2003).
Zhang et al., "Preclinical Experimental Models of Drug Metabolism and Disposition in Drug Discovery and Development", Acta Pharmaceutica Sinica B, 2(6):549-561 (2012).

\* cited by examiner

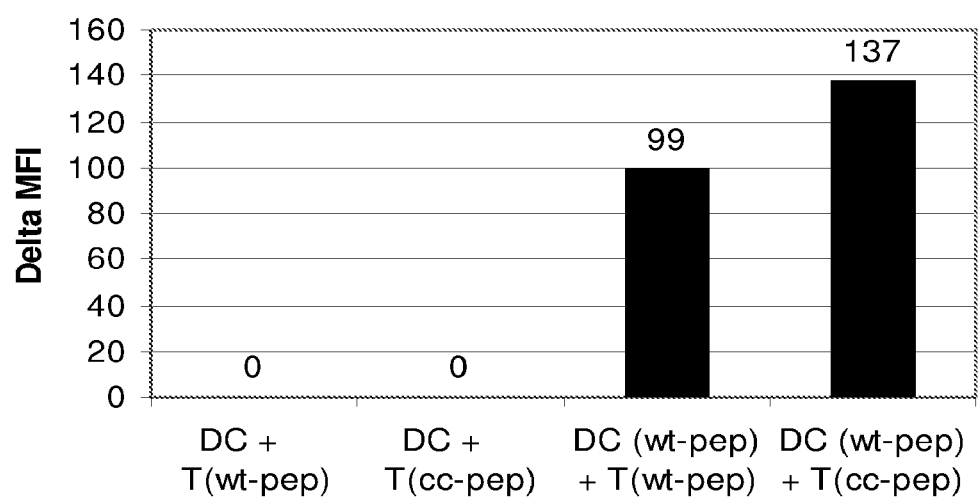

SEQUENCE LISTING

```
<160> NUMBER OF SEQ ID NOS: 41

<210> SEQ ID NO 1
<211> LENGTH: 10
<212> TYPE: PRT
<213> ORGANISM: Artificial Sequence
<220> FEATURE:
<223> OTHER INFORMATION: amino acids 912-921 of capsid protein
      adenovirus serotype 5

<400> SEQUENCE: 1

Pro Thr Leu Leu Tyr Val Leu Phe Glu Val
1               5                   10

<210> SEQ ID NO 2
<211> LENGTH: 14
<212> TYPE: PRT
<213> ORGANISM: Artificial Sequence
```

```
<220> FEATURE:
<223> OTHER INFORMATION: modified T-cell epitope of capsid protein
      adenovirus serotype 5
<220> FEATURE:
<221> NAME/KEY: MISC_FEATURE
<222> LOCATION: (1)..(4)
<223> OTHER INFORMATION: thioreductase motif

<400> SEQUENCE: 2

Cys His Gly Cys Pro Thr Leu Leu Tyr Val Leu Phe Glu Val
1               5                   10

<210> SEQ ID NO 3
<211> LENGTH: 9
<212> TYPE: PRT
<213> ORGANISM: Artificial Sequence
<220> FEATURE:
<223> OTHER INFORMATION: ESAT6 T-cell epitope of Mycobacterium
      tuberculosis

<400> SEQUENCE: 3

Phe Ala Gly Ile Glu Ala Ala Ala Ser
1               5

<210> SEQ ID NO 4
<211> LENGTH: 13
<212> TYPE: PRT
<213> ORGANISM: Artificial Sequence
<220> FEATURE:
<223> OTHER INFORMATION: modified ESAT6 T-cell epitope
<220> FEATURE:
<221> NAME/KEY: MISC_FEATURE
<222> LOCATION: (1)..(4)
<223> OTHER INFORMATION: thioreductase motif

<400> SEQUENCE: 4

Cys Gly His Cys Phe Ala Gly Ile Glu Ala Ala Ala Ser
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Th2R T-cell epitope Plasmodium falciparum

<400> SEQUENCE: 5

Asp Lys His Ile Glu Gln Tyr Leu Lys
1               5

<210> SEQ ID NO 6
<211> LENGTH: 13
<212> TYPE: PRT
<213> ORGANISM: Artificial Sequence
<220> FEATURE:
<223> OTHER INFORMATION: modified Th2R T-cell epitope
<220> FEATURE:
<221> NAME/KEY: MISC_FEATURE
<222> LOCATION: (1)..(4)
<223> OTHER INFORMATION: thioreductase motif

<400> SEQUENCE: 6

Cys Gly His Cys Asp Lys His Ile Glu Gln Tyr Leu Lys
1               5                   10

<210> SEQ ID NO 7
<211> LENGTH: 9
<212> TYPE: PRT
<213> ORGANISM: Artificial Sequence

```
<220> FEATURE:
<223> OTHER INFORMATION: amino acids 380-388 of CSP antigen Plasmodium
      falciparum

<400> SEQUENCE: 7

Glu Lys Lys Ile Cys Lys Met Glu Lys
1               5

<210> SEQ ID NO 8
<211> LENGTH: 13
<212> TYPE: PRT
<213> ORGANISM: Artificial Sequence
<220> FEATURE:
<223> OTHER INFORMATION: modified T-cell epitope of CSP antigen
      Plasmodium falciparum
<220> FEATURE:
<221> NAME/KEY: MISC_FEATURE
<222> LOCATION: (1)..(4)
<223> OTHER INFORMATION: modified T-cell epitope

<400> SEQUENCE: 8

Cys Gly His Cys Glu Lys Lys Ile Cys Lys Met Glu Lys
1               5                   10

<210> SEQ ID NO 9
<211> LENGTH: 9
<212> TYPE: PRT
<213> ORGANISM: Artificial Sequence
<220> FEATURE:
<223> OTHER INFORMATION: T-cell epitope of influenza hemagglutinin
      antigen

<400> SEQUENCE: 9

Lys Tyr Val Lys Gln Asn Thr Leu Lys
1               5

<210> SEQ ID NO 10
<211> LENGTH: 13
<212> TYPE: PRT
<213> ORGANISM: Artificial Sequence
<220> FEATURE:
<223> OTHER INFORMATION: modified T-cell epitope of influenza
      hemagglutinin antigen
<220> FEATURE:
<221> NAME/KEY: MISC_FEATURE
<222> LOCATION: (1)..(4)
<223> OTHER INFORMATION: thioreductase motif

<400> SEQUENCE: 10

Cys Gly His Cys Lys Tyr Val Lys Gln Asn Thr Leu Lys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: amino acids 163-171 of LACK

<400> SEQUENCE: 11

Glu His Pro Ile Val Val Ser Gly Ser
1               5

<210> SEQ ID NO 12
<211> LENGTH: 13
<212> TYPE: PRT
<213> ORGANISM: Artificial Sequence
<220> FEATURE:
<223> OTHER INFORMATION: modified T-cell epitope of LACK
```

```
<220> FEATURE:
<221> NAME/KEY: MISC_FEATURE
<222> LOCATION: (1)..(4)
<223> OTHER INFORMATION: thioreductase motif

<400> SEQUENCE: 12

Cys Gly His Cys Glu His Pro Ile Val Val Ser Gly Ser
1               5                   10

<210> SEQ ID NO 13
<211> LENGTH: 9
<212> TYPE: PRT
<213> ORGANISM: Artificial Sequence
<220> FEATURE:
<223> OTHER INFORMATION: amino acids 437-455 of the HIV gp120 subunit

<400> SEQUENCE: 13

Arg Ala Met Tyr Ala Pro Pro Ile Ala
1               5

<210> SEQ ID NO 14
<211> LENGTH: 13
<212> TYPE: PRT
<213> ORGANISM: Artificial Sequence
<220> FEATURE:
<223> OTHER INFORMATION: modified HIV T-cell epitope
<220> FEATURE:
<221> NAME/KEY: MISC_FEATURE
<222> LOCATION: (1)..(4)
<223> OTHER INFORMATION: thioreductase motif

<400> SEQUENCE: 14

Cys Gly His Cys Arg Ala Met Tyr Ala Pro Pro Ile Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (7)..(7)
<223> OTHER INFORMATION: Xaa denotes sequence of any T-cell epitope

<400> SEQUENCE: 15

Cys Xaa Xaa Cys Gly Gly Xaa
1               5

<210> SEQ ID NO 16
<211> LENGTH: 6
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (6)..(6)
<223> OTHER INFORMATION: Xaa denotes the sequence of any T-cell epitope
```

```
<400> SEQUENCE: 16

Cys Xaa Xaa Cys Gly Xaa
1               5

<210> SEQ ID NO 17
<211> LENGTH: 8
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (8)..(8)
<223> OTHER INFORMATION: Xaa denotes sequence of any T-cell epitope

<400> SEQUENCE: 17

Cys Xaa Xaa Cys Ser Ser Ser Xaa
1               5

<210> SEQ ID NO 18
<211> LENGTH: 9
<212> TYPE: PRT
<213> ORGANISM: Artificial Sequence
<220> FEATURE:
<223> OTHER INFORMATION: general sequence of peptide of the invention
<220> FEATURE:
<221> NAME/KEY: MISC_FEATURE
<222> LOCATION: (2)..(3)
<223> OTHER INFORMATION: Xaa at positions 2 and 3 denote any amino acid
<220> FEATURE:
<221> NAME/KEY: MISC_FEATURE
<222> LOCATION: (9)..(9)
<223> OTHER INFORMATION: Xaa denotes sequence of any T-cell epitope

<400> SEQUENCE: 18

Cys Xaa Xaa Cys Ser Gly Ser Gly Xaa
1               5

<210> SEQ ID NO 19
<211> LENGTH: 14
<212> TYPE: PRT
<213> ORGANISM: Artificial Sequence
<220> FEATURE:
<223> OTHER INFORMATION: thioreductase motif repeat
<220> FEATURE:
<221> NAME/KEY: MISC_FEATURE
<222> LOCATION: (1)..(14)
<223> OTHER INFORMATION: Xaa at positions 2, 3, 5, 7, 8, 10, 12, and 13
      denote any amino acid

<400> SEQUENCE: 19

Cys Xaa Xaa Cys Xaa Cys Xaa Xaa Cys Xaa Cys Xaa Xaa Cys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: thioreductase motif repeat
<220> FEATURE:
<221> NAME/KEY: MISC_FEATURE
<222> LOCATION: (1)..(12)
<223> OTHER INFORMATION: Xaa at positions 2, 3, 6, 7, 10, and 11 denote
      any amino acid
```

```
<400> SEQUENCE: 20

Cys Xaa Xaa Cys Cys Xaa Xaa Cys Cys Xaa Xaa Cys
1               5                  10

<210> S

```
<220> FEATURE:
<221> NAME/KEY: MISC_FEATURE
<222> LOCATION: (2)..(3)
<223> OTHER INFORMATION: Xaa at positions 2 and 3 denote any amino acid

<400> SEQUENCE: 24

Asp Xaa Xaa Leu Leu
1               5

<210> SEQ ID NO 25
<211> LENGTH: 6
<212> TYPE: PRT
<213> ORGANISM: Artificial Sequence
<220> FEATURE:
<223> OTHER INFORMATION: late endosome targeting signal
<220> FEATURE:
<221> NAME/KEY: MISC_FEATURE
<222> LOCATION: (2)..(5)
<223> OTHER INFORMATION: Xaa at positions 2, 3 and 4 denote any amino
      acid

<400> SEQUENCE: 25

Asp Xaa Xaa Xaa Leu Leu
1               5

<210> SEQ ID NO 26
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be Cys, Ser, or Thr

<400> SEQUENCE: 26

Cys Xaa Xaa Xaa
1

<210> SEQ ID NO 27
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Cys, Ser, or Thr
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 27

Xaa Xaa Xaa Cys
1

<210> SEQ ID NO 28
<211> LENGTH: 4
<212> TYPE: PRT
<213> ORGANISM: Artificial Sequence
<220> FEATURE:
<223> OTHER INFORMATION: redox motif
```

```
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 28

Cys Xaa Xaa Cys
1

<210> SEQ ID NO 29
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 29

Cys Xaa Xaa Ser
1

<210> SEQ ID NO 30
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 30

Cys Xaa Xaa Thr
1

<210> SEQ ID NO 31
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 31

Ser Xaa Xaa Cys
1

<210> SEQ ID NO 32
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 32

Ser Xaa Xaa Ser
1
```

-continued

```
<210> SEQ ID NO 33
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 33

Thr Xaa Xaa Cys
1

<210> SEQ ID NO 34
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Cys, or Ser

<400> SEQUENCE: 34

Cys Xaa Xaa Xaa
1

<210> SEQ ID NO 35
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Cys, or Ser
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 35

Xaa Xaa Xaa Cys
1

<210> SEQ ID NO 36
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Cys, Ser, or Thr
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Cys, Ser, or Thr
```

```
<400> SEQUENCE: 36

Xaa Xaa Xaa Xaa
1

<210> SEQ ID NO 37
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: MISC_FEATURE
<222> LOCATION: (2)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Ser, or Thr

<400> SEQUENCE: 37

Cys Xaa Xaa Xaa
1

<210> SEQ ID NO 38
<211> LENGTH: 4
<212> TYPE: PRT
<213> ORGANISM: Artificial Sequence
<220> FEATURE:
<223> OTHER INFORMATION: redox motif
<220> FEATURE:
<221> NAME/KEY: misc_feature
<222> LOCATION: (1)..(1)
<223> OTHER INFORMATION: Xaa can be Ser, or Thr
<220> FEATURE:
<221> NAME/KEY: MISC_FEATURE
<222> LOCATION: (2)..(3)
<223> OTHER INFORMATION: Xaa can be any naturally occurring amino acid

<400> SEQUENCE: 38

Xaa Xaa Xaa Cys
1

<210> SEQ ID NO 39
<211> LENGTH: 4
<212> TYPE: PRT
<213> ORGANISM: Artificial Sequence
<220> FEATURE:
<223> OTHER INFORMATION: late endosome targeting signal
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any amino acid with a bulky
      hydrophobic side chain, such as Phe, Tyr and Trp

<400> SEQUENCE: 39

Tyr Xaa Xaa Xaa
1

<210> SEQ ID NO 40
<211> LENGTH: 4
<212> TYPE: PRT
<213> ORGANISM: Artificial Sequence
<220> FEATURE:
<223> OTHER INFORMATION: redox motif
```

```
<400> SEQUENCE: 40

Cys Gly His Cys
1

<210> SEQ ID NO 41
<211> LENGTH: 4
<212> TYPE: PRT
<213> ORGANISM: Artificial Sequence
<220> FEATURE:
<223> OTHER INFORMATION: redox motif

<400> SEQUENCE: 41

Cys His Gly Cys
1
```

IMMUNOTHERAPY TARGETING INTRACELLULAR PATHOGENS

This application is a divisional of U.S. application Ser. No. 12/735,742, filed Aug. 13, 2010 (published as US 2012-0009678 A1), which is a U.S. National Phase of International Application No. PCT/EP2009/051808, filed Feb. 16, 2009, which claims benefit of U.S. Provisional Application No. 61/035,890, filed Mar. 12, 2008 and European Patent Application No. 08447009.5, filed Feb. 14, 2008, the entire contents of each of which is incorporated herein by reference.

REFERENCE TO A SEQUENCE LISTING SUBMITTED ELECTRONICALLY VIA EFS-WEB

The content of the electronically submitted sequence listing (Name: 2752_0108_Sequence_Listing, Size: 12,906 bytes; and Date of Creation: Apr. 15, 2019) is herein incorporated by reference in its entirety.

FIELD OF THE INVENTION

The present invention relates to immunogenic peptides and their use in preventing and/or treating infection with intracellular pathogens.

BACKGROUND OF THE INVENTION

Numerous infectious diseases are due to microorganisms with an essentially intracellular life cycle. Examples are viral diseases such as influenza, *mycobacterium* infections such as tuberculosis, bacterial infections such as *Mycoplasma* and parasitic diseases such as *Leishmania* and malaria.

Current vaccination procedures aiming at intracellular pathogens, when available, primarily elicit CD4+ T cells that are effective in helping B cells to produce specific antibodies, but cause no, or very little cytolytic activity. Hence, vaccine effectiveness remains limited.

Due to their intracellular location, these microorganisms are only marginally affected by humoral immunity and specific antibodies. An effective defence against intracellular infections depends on the elicitation of cellular immunity, namely of cells that recognise infected cells by virtue of presentation of microorganism-derived antigens into the context of MHC class I and class II antigens. Following recognition, immunocompetent cells are activated and destroy infected cells using a variety of mechanisms including exocytose of cytolytic enzymes and IFN-gamma induction of nitric oxide synthase (NOS). IFN-gamma activates the formation of reactive oxygen and reactive nitrogen intermediates, and induces the transcription of indolamine-2,3-dioxygenase (IDO) with subsequent deprivation in tryptophan. Tryptophan deprivation can severely affect the intracellular survival of bacterial pathogens such as Chlamydiae. In infections with *Candida*, fungal morphology and sensitivity to anti-fungal agents are profoundly affected by intracellular tryptophan concentrations (Bozza et al. (2005) *J. Immunol.* 174:2910-2918).

Reactive oxygen intermediates are generated by activation of NADPH oxidase elicited by bacterial products and IFN-gamma or IL-8. This activation elicits the formation of superoxide ($O_2^-$), which converts into $H_2O_2$ and hydroxyl anion ($OH^-$). Upon action of myeloperoxidase, hypochlorous acid (HOCl) and chloramine are formed. All these intermediates have potent anti-microbial and tumoricidal activities.

Inducible nitric oxide synthase (iNOS), as induced by IFN-gamma or TNF-alpha generates NO radicals, which can be converted into peroxynitrite (ONOO—) or nitrothiols. NO radicals exert potent microbicidal effects. iNOS is under transcriptional control by factors such as NFk-B and the Jak/STAT complex. NO directly or indirectly influences the life cycle of viruses, bacteria and parasites. Thus, for example, S-nitrosylation of the cysteine protease 3C of Coxsackie virus interrupts the viral life cycle (Saura et al. (1999) *Immunity* 10:21-28). The production of $O_2^-$ by *Helicobacter pylori* leads to microbicidal peroxinitrite by interaction with host NO (Nagata et al. (1998) *J. Biol. Chem.* 273:14071-14073). Conversely, absence of enzyme participating in the elaboration of reactive intermediates, such as for the defect in myeloperoxidase leads to the development of chronic fungal infections, such as *Candida albicans* (Nguyen and Katner (1997) *Clin. Infect. Dis.* 24:258-260). The above pathways converge towards the elimination of both extracellular and intracellular pathogens and are triggered by IFN-gamma. A source of IFN-gamma providing high concentrations at sites of infection therefore provides a potential benefit in the elimination of such pathogens. A more optimal strategy to fight intracellular pathogens could be to combine non-specific intracellular microbicidal mechanisms with specific adaptive immunity. An example would be to design a system by which high concentrations of IFN-gamma would be delivered precisely at sites of infection, so as to avoid systemic side-effects of pro-inflammatory cytokines.

SUMMARY OF THE INVENTION

The present invention relates to the use of isolated immunogenic peptides for preventing or treating a subject suffering from infection with an intracellular pathogen and for inducing in said subject CD4+ regulatory T cells which stimulate non-specific intracellular microbicidal mechanisms in cells of the subject infected with the intracellular pathogen.

The present invention relates in one aspect to the use of at least one isolated immunogenic peptide comprising (i) a T-cell epitope derived from an intracellular pathogen-associated antigen and (ii) a [CST]-(X)2-[CST] (SEQ ID NO: 36) motif, more particularly a C-(X)2-[CST] (SEQ ID NO: 26) or [CST]-(X)2-C (SEQ ID NO: 27) motif, for the manufacture of a medicament for preventing or treating, in a subject, infection with said intracellular pathogen.

In a further aspect, the invention also covers the use of at least one isolated immunogenic peptide comprising (i) a T-cell epitope derived from an intracellular pathogen-associated antigen and (ii) a [CST]-(X)2-[CST] (SEQ ID NO: 36) motif, more particularly a C-(X)2-[CST] (SEQ ID NO: 26) or [CST]-(X)2-C (SEQ ID NO: 27) motif, for the manufacture of a medicament for inducing in a subject CD4+ regulatory T cells which are stimulating non-specific intracellular microbicidal mechanisms in cells of said subject infected with said intracellular pathogen.

Generally, the invention provides immunogenic peptides comprising (i) a T-cell epitope derived from an intracellular pathogen-associated antigen and (ii) C-(X)2-[CST] (SEQ ID NO: 26) or [CST]-(X)2-C(SEQ ID NO: 27) motif for use in preventing or treating a subject suffering from infection with an intracellular pathogen and for inducing in said subject CD4+ regulatory T cells which stimulate non-specific intracellular microbicidal mechanisms in cells of the subject infected with the intracellular pathogen.

In any of the above uses said intracellular pathogen-associated antigen may be any antigen derived from viruses, bacteria, mycobacteria or parasites with an intracellular life cycle.

In any of the above uses, said C-(X)2-[CST] (SEQ ID NO: 26) or [CST]-(X)2-C(SEQ ID NO: 27) motif in said immunogenic peptide may be adjacent to said T-cell epitope, or separated from said T-cell epitope by a linker. In particular, said linker consists of at most 7 amino acids.

In a particular embodiments of the immunogenic peptides for use in the above applications, said C-(X)2-[CST] (SEQ ID NO: 26) or [CST]-(X)2-C(SEQ ID NO: 27) motif does not naturally occur within a region of 11 amino acids N- or C-terminally adjacent to the T-cell epitope in the intracellular pathogen-associated antigen. In particular said C-(X)2-[CST] (SEQ ID NO: 26) or [CST]-(X)2-C(SEQ ID NO: 27) motif is positioned N-terminally of the T-cell epitope. Further in particular, at least one X in said [CST]-(X)2-[CST] (SEQ ID NO: 36) motif is Gly, Ala, Ser or Thr, additionally or alternatively at least on X is His or Pro. In particular embodiments at least one C in said C-(X)2-[CST] (SEQ ID NO: 26) or [CST]-(X)2-C (SEQ ID NO: 27) motif is methylated.

In particular embodiments of the immunogenic peptide for use in the above applications, said immunogenic peptide further comprises an endosomal targeting sequence. Any of the above immunogenic peptides may be produced by chemical synthesis or by recombinant expression.

A further aspect of the invention relates to methods for obtaining a population of intracellular pathogen-associated antigen-specific regulatory T cells with cytotoxic properties, said methods comprising the steps of:
  providing peripheral blood cells;
  contacting said cells with an immunogenic peptide comprising (i) a T-cell epitope derived from an intracellular pathogen-associated antigen and (ii) a [CST]-(X)2-[CST] (SEQ ID NO: 36), more particularly a C-(X)2-[CST] (SEQ ID NO: 26) or [CST]-(X)2-C(SEQ ID NO: 27) motif; and
  expanding said cells in the presence of IL-2.

A further method of the invention aims at obtaining a population of intracellular pathogen-associated antigen-specific regulatory T cells with cytotoxic properties, and such methods comprise the steps of:
  providing an immunogenic peptide comprising (i) a T-cell epitope derived from an intracellular pathogen-associated antigen and (ii) a C-(X)2-[CST] (SEQ ID NO: 26) or [CST]-(X)2-C(SEQ ID NO: 27) motif;
  administering said immunogenic peptide to a subject; and
  obtaining said population of intracellular pathogen-associated antigen-specific regulatory T cells from said subject.

Populations of intracellular pathogen-associated antigen-specific regulatory T cells with cytotoxic properties obtainable by the above methods are also part of the invention, as well as their use for the manufacture of a medicament for preventing or treating, in a subject, infection with said intracellular pathogen.

A further aspect of the invention relates to isolated immunogenic peptides comprising a T-cell epitope from an intracellular pathogen-associated antigen and, adjacent to said T-cell epitope or separated from said T-cell epitope by a linker, a [CST]-(X)2-[CST] (SEQ ID NO: 36) motif, more particularly a C-(X)2-[CST] (SEQ ID NO: 26) or [CST]-(X)2-C(SEQ ID NO: 27) motif.

FIGURE LEGEND

FIG. 1 shows reactive oxygen species produced by dendritic cells after administration of T cells incubated with natural and modified T cell epitopes The bars in this FIGURE illustrate the change in intracellular production of reactive oxygen species (ROI) of dendritic cells incubated under different conditions and evaluated by Facs analysis of CDFDA oxidation ("delta MFI"=MFI=mean fluorescence intensity).
  DC+T (wt-pep): dendritic cells incubated with T cells expanded with natural (wild-type) T-cell epitope [SEQ ID. NO: 1] derived from adenovirus;
  DC+T (cc-pep): dendritic cells incubated with T cells expanded with T-cell epitope derived from adenovirus, wherein said T-cell epitope is modified by attaching the amino acids CHGC (SEQ ID NO: 41) to the N-terminus of the epitope [SEQ ID. NO: 2];
  DC (wt-pep)+T (wt-pep): dendritic cells incubated with natural T-cell epitope [SEQ ID. NO: 1] derived from adenovirus and with T cells expanded with natural T-cell epitope [SEQ ID. NO: 1]
  DC (wt-pep)+T (cc-pep): dendritic cells incubated with natural T-cell epitope [SEQ ID. NO: 1] derived from adenovirus and with T cells expanded with modified T-cell epitope [SEQ ID. NO: 2], (modification as in "DC+T (cc-pep)");
See Example 1 for details on the T-cell epitopes.

DETAILED DESCRIPTION OF THE INVENTION

Definitions

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The term "epitope" when used herein refers to one or several portions (which may define a conformational epitope) of a protein or factor which is/are specifically recognised and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) (eliciting an immune response only when attached to a carrier) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide"

The term "T cell epitope" or "T-cell epitope" in the context of the present invention refers to a dominant, sub-dominant or minor T cell epitope, i.e., a part of an antigenic protein or factor that is specifically recognised and bound by a receptor at the cell surface of a T lymphocyte. Whether an epitope is dominant, sub-dominant or minor depends on the immune reaction elicited against the epitope. Dominance depends on the frequency at which such epitopes are recognised by T cells and able to activate them, among all the possible T cell epitopes of a protein. In particular, a T cell epitope is an epitope bound by MHC class I or MHC class II molecules.

The term "MHC" refers to "major histocompatibility antigen". In humans, the MHC genes are known as HLA ("human leukocyte antigen") genes. Although there is no consistently followed convention, some literature uses HLA to refer to HLA protein molecules, and MHC to refer to the genes encoding the HLA proteins. As such the terms "MHC" and "HLA" are equivalents when used herein. The HLA system in man has its equivalent in the mouse, i.e., the H2 system. The most intensely-studied HLA genes are the nine so-called classical MHC genes: HLA-A, HLA-B, HLA-C, HLA-DPA1, HLA-DPB1, HLA-DQA1, HLA-DQB1, HLA-DRA, and HLA-DRB1. In humans, the MHC is divided into three regions: Class I, II, and III. The A, B, and C genes belong to MHC class I, whereas the six D genes belong to class II. MHC class I molecules are made of a single polymorphic chain containing 3 domains (alpha 1, 2 and 3), which associates with beta 2 microglobulin at cell surface. Class II molecules are made of 2 polymorphic chains, each containing 2 chains (alpha 1 and 2, and beta 1 and 2).

Class I MHC molecules are expressed on virtually all nucleated cells. Peptide fragments presented in the context of class I MHC molecules are recognised by CD8+T lymphocytes (cytotoxic T lymphocytes or CTLs). CD8+T lymphocytes frequently mature into cytotoxic effectors which can lyse cells bearing the stimulating antigen. Class II MHC molecules are expressed primarily on activated lymphocytes and antigen-presenting cells. CD4+T lymphocytes (helper T lymphocytes or HTLs) are activated with recognition of a unique peptide fragment presented by a class II MHC molecule, usually found on an antigen presenting cell like a macrophage or dendritic cell. CD4+T lymphocytes proliferate and secrete cytokines that either support an antibody-mediated response through the production of IL-4 and IL-10 or support a cell-mediated response through the production of IL-2 and IFN-gamma.

Functional HLAs are characterised by a deep binding groove to which endogenous as well as foreign, potentially antigenic peptides bind. The groove is further characterised by a well-defined shape and physico-chemical properties. HLA class I binding sites are closed, in that the peptide termini are pinned down into the ends of the groove. They are also involved in a network of hydrogen bonds with conserved HLA residues. In view of these restraints, the length of bound peptides is limited to 8-10 residues. However, it has been demonstrated that peptides of up to 12 amino acid residues are also capable of binding HLA class I. Superposition of the structures of different HLA complexes confirmed a general mode of binding wherein peptides adopt a relatively linear, extended conformation.

In contrast to HLA class I binding sites, class II sites are open at both ends. This allows peptides to extend from the actual region of binding, thereby "hanging out" at both ends. Class II HLAs can therefore bind peptide ligands of variable length, ranging from 9 to more than 25 amino acid residues. Similar to HLA class I, the affinity of a class II ligand is determined by a "constant" and a "variable" component. The constant part again results from a network of hydrogen bonds formed between conserved residues in the HLA class II groove and the main-chain of a bound peptide. However, this hydrogen bond pattern is not confined to the N- and C-terminal residues of the peptide but distributed over the whole chain. The latter is important because it restricts the conformation of complexed peptides to a strictly linear mode of binding. This is common for all class II allotypes. The second component determining the binding affinity of a peptide is variable due to certain positions of polymorphism within class II binding sites. Different allotypes form different complementary pockets within the groove, thereby accounting for subtype-dependent selection of peptides, or specificity. Importantly, the constraints on the amino acid residues held within class II pockets are in general "softer" than for class I. There is much more cross reactivity of peptides among different HLA class II allotypes. The sequence of the +/−9 amino acids of an MHC class II T cell epitope that fit in the groove of the MHC II molecule are usually numbered P1 to P9. Additional amino acids N-terminal of the epitope are numbered P−1, P−2 and so on, amino acids C-terminal of the epitope are numbered P+1, P+2 and so on.

The term "organic compound having a reducing activity" when used herein refers to compounds, more in particular amino acid sequences, capable of reducing disulfide bonds in proteins. An alternatively used term for these amino acid sequences is "redox motif".

The term "therapeutically effective amount" refers to an amount of the peptide of the invention or derivative thereof, which produces the desired therapeutic or preventive effect in a patient. For example, in reference to a disease or disorder, it is the amount which reduces to some extent one or more symptoms of the disease or disorder, and more particularly returns to normal, either partially or completely, the physiological or biochemical parameters associated with or causative of the disease or disorder. According to one particular embodiment of the present invention, the therapeutically effective amount is the amount of the peptide of the invention or derivative thereof, which will lead to an improvement or restoration of the normal physiological situation. For instance, when used to therapeutically treat a mammal affected by an immune disorder, it is a daily amount peptide/kg body weight of the said mammal. Alternatively, where the administration is through gene-therapy, the amount of naked DNA or viral vectors is adjusted to ensure the local production of the relevant dosage of the peptide of the invention, derivative or homologue thereof.

The term "natural" when used herein is referring to a sequence relates to the fact that the sequence is identical to a naturally occurring sequence or is identical to part of such naturally occurring sequence. In contrast therewith the term "artificial" refers to a sequence which as such does not occur in nature. Unless otherwise specified, the terms natural and artificial referring to a sequence thus exclusively relate to a particular amino acid (or nucleotide) sequence (e.g. the sequence of the immunogenic peptide, a sequence comprised within the immunogenic peptide in epitope sequence) and do not refer to the nature of the immunogenic peptide as such. Optionally, an artificial sequence is obtained from a natural sequence by limited modifications such as changing one or more amino acids within the naturally occurring sequence or by adding amino acids N- or C-terminally of a naturally occurring sequence. Amino acids are referred to herein with their full name, their three-letter abbreviation or their one letter abbreviation. Motifs of amino acid sequences are written herein according to the format of Prosite (Hula et al. (2006) *Nucleic Acids Res.* 34 (Database issue D227-D230). The symbol X is used for a position where any amino acid is accepted. Alternatives are indicated by listing the acceptable amino acids for a given position, between square brackets ('[ ]'). For example: [CST] stands for an amino acid selected from Cys, Ser or Thr. Amino acids which are excluded as alternatives are indicated by listing them between curly brackets ('{ }'). For example: {AM} stands for any amino acid except Ala and Met. The different elements in a motif are separated from each other by a hyphen -. Repetition of an identical element within a motif can be indicated by placing behind that element a numerical value or a numerical range between parentheses. For example: X(2) corresponds to X-X, X(2, 4) corresponds to X-X or X-X-X or X-X-X-X, A(3) corresponds to A-A-A.

The term "homologue" when used herein with reference to the epitopes used in the context of the invention, refer to molecules having at least 50%, at least 70%, at least 80%, at least 90%, at least 95% or at least 98% amino acid sequence identity with the naturally occurring epitope, thereby maintaining the ability of the epitope to bind an antibody or cell surface receptor of a B and/or T cell. Particular embodiments of homologues of an epitope correspond to the natural epitope modified in at most three, more particularly in at most two, most particularly in one amino acid.

The term "derivative" when used herein with reference to the peptides of the invention refers to molecules which contain at least the peptide active portion (i.e. capable of eliciting cytolytic CD4+ T cell activity) and, in addition thereto comprises a complementary portion which can have different purposes such as stabilising the peptides or altering the pharmacokinetic or pharmacodynamic properties of the peptide.

The term "sequence identity" of two sequences when used herein relates to the number of positions with identical nucleotides or amino acids divided by the number of nucleotides or amino acids in the shorter of the sequences, when the two sequences are aligned. In particular embodiments, said sequence identity is from 70% to 80%, from 81% to 85%, from 86% to 90%, from 91% to 95%, from 96% to 100%, or 100%.

The terms "peptide-encoding polynucleotide (or nucleic acid)" and "polynucleotide (or nucleic acid) encoding peptide" when used herein refer to a nucleotide sequence, which, when expressed in an appropriate environment, results in the generation of the relevant peptide sequence or a derivative or homologue thereof. Such polynucleotides or nucleic acids include the normal sequences encoding the peptide, as well as derivatives and fragments of these nucleic acids capable of expressing a peptide with the required activity. According to one embodiment, the nucleic acid encoding the peptides according to the invention or fragment thereof is a sequence encoding the peptide or fragment thereof originating from a mammal or corresponding to a mammalian, most particularly a human peptide fragment.

DETAILED DESCRIPTION

The invention is based on the unexpected finding that the stimulation of pathogen-specific CD4+T lymphocytes with peptides encompassing a T-cell epitope and a consensus sequence with thioreductase activity elicit the maturation and expansion of a new subset of CD4+ T cells. Such cells have the capacity to induce apoptosis in antigen-presenting cells (APC) only when activated by cognate interaction with MHC class II presented peptides. Besides, CD4+ T cells produce large amounts of IFN-gamma, with activation of the formation of reactive oxygen and reactive nitrogen intermediates in APC, as well as activation of IDO (indolamine-2, 3-dioxygenase). The new CD4+ subset is also characterised by high surface expression of CTLA-4, endowed with further capacity to induce IDO.

The invention therefore provides compounds and methods to produce and to use such compounds in the setting of infections caused by intracellular pathogens. The local delivery of high concentration of IFN-gamma maximises the non-specific microbicidal mechanisms whilst avoiding systemic side-effects. In particular a methodology is envisaged by which specific CD4+ T cells are turned into potent cytolytic cells, while keeping full specificity for the microorganism-derived antigen. The consequence is two-fold:

(1) induction of intracellular microbicidal activity through the production of IFN-gamma and reverse signalling mediated by the interaction between CTLA 4 on cytotoxic CD4+ T cells and B7 at the APC surface, resulting in induction of oxidative and nitrogen radicals toxic for microorganism, and deprivation of tryptophan through IDO induction;

(2) rapid elimination of cells by induction of apoptosis at an early stage after infection, thereby aborting infection.

Thus, in one aspect the invention relates to the use of at least one isolated immunogenic peptide comprising (i) a T-cell epitope derived from an intracellular pathogen-associated antigen and (ii) a C-(X)2-[CST] (SEQ ID NO: 26) or [CST]-(X)2-C(SEQ ID NO: 27) motif, for the manufacture of a medicament for preventing or treating, in a subject, infection with said intracellular pathogen. Hence, the immunogenic peptide(s) or the medicament comprising them can be used for prior or prophylactic treatment or immunisation of a subject in order to avoid/abort subsequent/de novo infection with an intracellular pathogen. Likewise, the immunogenic peptides or the medicament comprising them can be used for therapeutic treatment or immunisation of a subject infected with an intracellular pathogen. The treatment must not necessarily result in "sterilisation" of the immunised subject, i.e., complete eradication/elimination of the pathogen from the subject. Hence, it is accepted that for some diseases it is wishful to avoid the development of a chronic state and it is accepted that the acute phase of that disease most likely cannot be avoided. Likewise, in an already infected subject, the aim of the treatment may be to achieve a substantial decrease/lowering of the pathogenic load in that subject.

In a further aspect, the invention also covers the use of at least one isolated immunogenic peptide comprising (i) a T-cell epitope derived from an intracellular pathogen-associated antigen and (ii) a C-(X)2-[CST] (SEQ ID NO: 26) or [CST]-(X)2-C(SEQ ID NO: 27) motif, for the manufacture of a medicament for inducing in a subject CD4+ regulatory T cells which stimulate non-specific intracellular microbicidal mechanisms in cells of said subject infected with said intracellular pathogen.

In the above uses, the immunogenic peptide(s) or the medicament comprising them can be used for prior or prophylactic treatment or immunisation of a subject in order to induce a normally unexpected activation in the immunised subject CD4+ regulatory T cells which stimulate non-specific intracellular microbicidal mechanisms in cells of said subject that are de novo/subsequently infected with the intracellular pathogen. Likewise, the immunogenic peptides or the medicaments comprising them can be used for therapeutic treatment or immunisation of a subject in order to induce a normally unexpected activation in the immunised subject CD4+ regulatory T cells which stimulate non-specific intracellular microbicidal mechanisms in cells of said subject infected with the intracellular pathogen. In particular, such non-specific intracellular microbicidal mechanisms include the induction of reactive oxygen and nitrogen intermediates, induction of IDO and deprivation of amino acids essential for pathogen survival such as tryptophan. Further-more, said CD4+ regulatory T cells display increased transcription of IFN-gamma and granzymes (which contribute to their microbicidal cytotoxic properties) and overexpression of surface CTLA-4. The production of IFN-gamma elicits in the target cell the production of reactive oxygen and reactive nitrogen intermediates. Reverse signalling induced by cell contact between CTLA-4 on the CD4+ regulatory T cells and B7 molecules at the surface of target cells induces, together with IFNgamma, an increased production of IDO with subsequent degradation of tryptophan.

In addition, the above CD4+ regulatory T cells acquire cytotoxic properties for the cell presenting a T-cell epitope derived from an intracellular pathogen-associated antigen. Antigen-presenting cells can be conventional cells such as dendritic cells, macrophages or B lymphocytes, but also activated T lymphocytes or other cells which upon activation expressed MHC class II determinants.

It is important to realise that the kinetics of induction of intracellular microbicidal activity is fast and takes a few minutes to a few hours. On the contrary, the induction of apoptosis of target cells takes 6 to 24 hours. These two mechanisms of pathogen elimination are therefore acting in sequence rather than together.

In any of the uses described hereinabove, the subject or recipient is a mammal, in particular a (non-human) primate or a human.

In any of the above uses the intracellular pathogen-associated antigen may be any antigen derived from viruses, bacteria, mycobacteria or parasites with an intracellular life cycle. Viruses include ssDNA, dsDNA and RNA viruses, with as examples Herpesviridae, Flaviviridae and Picornaviridae, influenza, measles and immunodeficiency viruses. Bacteria and mycobacteria include *Mycobacterium tuberculosis*, and other mycobacteria pathogenic for humans or animals such as Yersiniae, Brucellae, Chlamydiae, Mycoplasmae, Rickettsiae, Salmonellae and Shigellae. Parasites include Plasmodiums, Leishmanias, Trypanosomas, *Toxoplasma gondii*, *Listeria* sp., *Histoplasma* sp.

The CD4+ regulatory T cells elicited by the immunogenic peptides of the present invention can suppress immune responses to even complex intracellular pathogen-associated antigens. A minimum requirement for such cells to be activated is to recognise a cognate peptide presented by MHC class II determinants, leading to apoptosis of the APC, thereby suppressing the responses of T cells (both CD4+ and CD8+ T cells) to all T cell epitopes presented by the APC.

There are situations in which more than one intracellular pathogen-associated antigen is present in a subject. Under such circumstances, the same APC may not present all relevant intracellular pathogen-associated antigens, as some of such antigens may be taken up by potentially different APCs. It is therefore anticipated that combination of two or more immunogenic peptides may be used for the prevention or treatment of infection with an intracellular pathogen.

A further aspect of the invention relates to methods and uses as described hereinabove wherein said one or more immunogenic peptides are replaced by CD4+ regulatory T-cell populations primed with the immunogenic peptides, or by one or more nucleotide sequence encoding the immunogenic peptide (e.g. in the form of naked DNA or a viral vector to be administered to an individual instead of the immunogenic peptide).

In particular embodiments, a combination of multiple immunogenic peptides (or T cell populations), i.e. more than 1 (e.g., 2, 3, 4, 5, 6, 7, 8, 9, 10 or more), can be used in any of the above.

These aspects of the invention, as well as the further modification of the immunogenic peptide are described in detail hereafter.

The present invention is based upon the finding that an immunogenic peptide, comprising a T cell epitope derived from an intracellular pathogen-associated antigen and a peptide sequence having reducing activity is capable of generating a population of CD4+ regulatory T cells, which have a cytotoxic effect on antigen presenting cells.

Accordingly, the invention relates to immunogenic peptides, which comprise at least one T-cell epitope of an intracellular pathogen-associated antigen with a potential to trigger an immune reaction, coupled to an organic compound having a reducing activity, such as a peptide with a thioreductase sequence motif. The T cell epitope and the organic compound are optionally separated by a linker (e.g. an organic spacer molecule or a peptide sequence). In further optional embodiments the immunogenic peptide additionally comprises an endosome targeting sequence (e.g. late endosomal targeting sequence) and/or additional "flanking" sequences.

The immunogenic peptides of the invention can be schematically represented as ALB or BLA, wherein A represents a T-cell epitope of an antigen (self or non-self) with a potential to trigger an immune reaction, L represents a linker and B represents an organic compound having a reducing activity.

The reducing activity of an organic compound can be assayed for its ability to reduce a sulfhydryl group such as in the insulin solubility assay known in the art, wherein the solubility of insulin is altered upon reduction, or with a fluorescence-labelled insulin. The reducing organic compound may be coupled at the amino-terminus side of the T-cell epitope or at the carboxy-terminus of the T-cell epitope.

Generally the organic compound with reducing activity is a peptide. Peptide fragments with reducing activity are encountered in thioreductases which are small disulfide reducing enzymes including glutaredoxins, nucleoredoxins, thioredoxins and other thiol/disulfide oxidoreductases They exert reducing activity for disulfide bonds on proteins (such as enzymes) through redox active cysteines within conserved active domain consensus sequences: C-X(2)-C(SEQ ID NO: 28), C-X(2)-S(SEQ ID NO: 29), C-X(2)-T (SEQ ID NO: 30), S-X(2)-C(SEQ ID NO: 31), T-X(2)-C(SEQ ID NO: 33) (Fomenko et al. (2003) Biochemistry 42, 11214-11225), in which X stands for any amino acid. Such domains are also found in larger proteins such as protein disulfide isomerase (PDI) and phosphoinositide-specific phospholipase C.

Accordingly, in particular embodiments, immunogenic peptides for use in accordance with the present invention comprise as redox motif the thioreductase sequence motif C-X(2)-[CST] (SEQ ID NO: 26) or [CST]-(X)2-C(SEQ ID NO: 27). In a further embodiment, the C-(X)2-[CST] (SEQ ID NO: 26) or [CST]-(X)2-C (SEQ ID NO: 27) motif is positioned N-terminally of the T-cell epitope. More specifically, in said redox motif at least one of the [CST] positions is occupied by a Cys; thus the motif is either C-X(2)-[CST] (SEQ ID NO: 26) or [CST]-X(2)-C (SEQ ID NO: 27). In the present application such a tetrapeptide will be referred to as "the motif". In particular embodiments immunogenic peptides of the invention contain the sequence motif C-X(2)-[CS] (SEQ ID NO: 34) or [CS]-X(2)-C (SEQ ID NO: 35). In more particular embodiments peptides contain the sequence motif C-X(2)-S(SEQ ID NO: 29), S-X(2)-C(SEQ ID NO: 31) or C-X(2)-C (SEQ ID NO: 28).

As explained in detail further on, the immunogenic peptides of the present invention can be made by chemical synthesis, which allows the incorporation of non-natural amino acids. Accordingly, in the motif of reducing compounds according to particular embodiments of the present invention, C represents either cysteine or another amino acids with a thiol group such as mercaptovaline, homocysteine or other natural or non-natural amino acids with a thiol function. In order to have reducing activity, the cysteines present in the motif should not occur as part of a cysteine disulfide bridge. Nevertheless, the motif may comprise modified cysteines such as methylated cysteine, which is converted into cysteine with free thiol groups in vivo.

Each of the amino acids X in the C-X(2)-[CST] (SEQ ID NO: 26) or [CST]-X(2)-C(SEQ ID NO: 27) motif of particular embodiments of the immunogenic peptides of the invention can be any natural amino acid, including S, C, or T or can be a non-natural amino acid, whereby the two amino acids X are either the same or different. In particular embodiments X is an amino acid with a small side chain such as Gly, Ala, Ser or Thr. In further particular embodiments, X is not an amino acid with a bulky side chain such as Tyr. In further particular embodiments at least one X in the [CST]-X(2)-[CST] (SEQ ID NO: 36) motif is His or Pro.

In the immunogenic peptides of the present invention comprising the (redox) motif described above, the motif is located such that, when the epitope fits into the MHC groove, the motif remains outside of the MHC binding groove. The motif is placed either immediately adjacent to the epitope sequence within the immunogenic peptide, or is separated from the T cell epitope by a linker. More particularly, the linker comprises an amino acid sequence of 7 amino acids or less. Most particularly, the linker comprises 1, 2, 3, or 4 amino acids. Alternatively, a linker may comprise 6, 8 or 10 amino acids. Typical amino acids used in linkers are serine and threonine. Example of peptides with linkers in accordance with the present invention are CXXC-G-epitope (SEQ ID NO:15), CXXC-GG-epitope (SEQ ID NO:16), CXXC-SSS-epitope (SEQ ID NO:17), CXXC-SGSG-epitope (SEQ ID NO:18) and the like.

In those particular embodiments of the peptides of the invention where the motif sequence is adjacent to the epitope sequence this is indicated as position P−4 to P−1 or P+1 to P+4 compared to the epitope sequence. Apart from a peptide linker other organic compounds can be used as linker to link the parts of the immunogenic peptide to each other.

The immunogenic peptides of the present invention can further comprise additional short amino acid sequences N or C-terminally of the (artificial) sequence comprising the T cell epitope and the reducing compound (motif). Such an amino acid sequence is generally referred to herein as a 'flanking sequence'. A flanking sequence can be positioned N- and/or C-terminally of the redox motif and/or of the T-cell epitope in the immunogenic peptide. When the immunogenic peptide comprises an endosomal targeting sequence, a flanking sequence can be present between the epitope and an endosomal targeting sequence and/or between the reducing compound (e.g. motif) and an endosomal targeting sequence. More particularly a flanking sequence is a sequence of up to 10 amino acids, or of in between 1 and 7 amino acids, such as a sequence of 2 amino acids.

In particular embodiments of the invention, the redox motif in the immunogenic peptide is located N-terminally from the epitope.

In further particular embodiments, where the redox motif present in the immunogenic peptide contains one cysteine, this cysteine is present in the motif in the position most remote from the epitope, thus the motif occurs as C-X(2)-[ST] (SEQ ID NO: 37) or C-X(2)-S(SEQ ID NO: 29) N-terminally of the epitope or occurs as [ST]-X(2)-C(SEQ ID NO: 38) or S-X(2)-C(SEQ ID NO: 31) carboxy-terminally of the epitope.

In certain embodiments of the present invention, immunogenic peptides are provided comprising one epitope sequence and a motif sequence. In further particular embodiments, the motif occurs several times (1, 2, 3, 4 or even more times) in the peptide, for example as repeats of the motif which can be spaced from each other by one or more amino acids (e.g. CXXC X CXXC X CXXC; SEQ ID NO:19), as repeats which are adjacent to each other (CXXC CXXC CXXC; SEQ ID NO:20) or as repeats which overlap with each other CXXCXXCXXC (SEQ ID NO:21) or CXCCXCCXCC (SEQ ID NO:22)). Alternatively, one or more motifs are provided at both the N and the C terminus of the T cell epitope sequence. Other variations envisaged for the immunogenic peptides of the present invention include peptides containing repeats of a T cell epitope sequence or multiple different T-cell epitopes wherein each epitope is preceded and/or followed by the motif (e.g. repeats of "motif-epitope" or repeats of "motif-epitope-motif"). Herein the motifs can all have the same sequence but this is not obligatory. It is noted that repetitive sequences of peptides which comprise an epitope which in itself comprises the motif will also result in a sequence comprising both the 'epitope' and a 'motif'. In such peptides, the motif within one epitope sequence functions as a motif outside a second epitope sequence. In particular embodiments however, the immunogenic peptides of the present invention comprise only one T cell epitope.

As described above the immunogenic peptides according to the invention comprise, in addition to a reducing compound/motif, a T cell epitope derived from an intracellular pathogen-associated antigen. A T cell epitope in a protein sequence can be identified by functional assays and/or one or more in silico prediction assays. The amino acids in a T cell epitope sequence are numbered according to their position in the binding groove of the MHC proteins. In particular embodiments, the T-cell epitope present within the peptides of the invention consists of between 8 and 25 amino acids, yet more particularly of between 8 and 16 amino acids, yet most particularly consists of 8, 9, 10, 11, 12, 13, 14, 15 or 16 amino acids. In a more particular embodiment, the T cell epitope consists of a sequence of 9 amino acids. In a further particular embodiment, the T-cell epitope is an epitope, which is presented to T cells by MHC-class II molecules. In particular embodiments of the present invention, the T cell epitope sequence is an epitope sequence which fits into the cleft of an MHC II protein, more particularly a nonapeptide fitting into the MHC II cleft. The T cell epitope of the immunogenic peptides of the invention can correspond either to a natural epitope sequence of a protein or can be a modified version thereof, provided the modified T cell epitope retains its ability to bind within the MHC cleft, similar to the natural T cell epitope sequence. The modified T cell epitope can have the same binding affinity for the MHC protein as the natural epitope, but can also have a lowered affinity. In particular embodiments the binding affinity of the modified peptide is no less than 10-fold less than the original peptide, more particularly no less than 5 times less. It is a finding of the present invention that the peptides of the present invention have a stabilising effect on protein complexes. Accordingly, the stabilising effect of the peptide MHC complex compensates for the lowered affinity of the modified epitope for the MHC molecule.

In particular embodiments, the immunogenic peptides of the invention further comprise an amino acid sequence (or another organic compound) facilitating uptake of the peptide into (late) endosomes for processing and presentation within MHC class II determinants. The late endosome targeting is mediated by signals present in the cytoplasmic tail of proteins and correspond to well-identified peptide motifs such as the dileucine-based [DE]XXXL[LI] (SEQ ID NO:23) or DXXLL (SEQ ID NO:24) motif (e.g. DXXXLL; SEQ ID NO:25), the tyrosine-based YXXØ (SEQ ID NO: 39) motif or the so-called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by MHC-class II molecules. Such endosomal targeting sequences are contained, for example, within the gp75 protein (Vijayasaradhi et al. (1995) *J Cell Biol* 130, 807-820), the human CD3 gamma protein, the HLA-BM β (Copier et al. (1996) *J. Immunol.* 157, 1017-1027), the cytoplasmic tail of the DEC205 receptor (Mahnke et al. (2000) *J Cell Biol* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the T cell response towards the intracellular pathogen-associated antigen-derived T cell epitope.

The immunogenic peptides of the invention can be generated by coupling a reducing compound, more particularly a reducing motif as described herein, N-terminally or C-terminally to a T-cell epitope of an intracellular pathogen-associated antigen (either directly adjacent thereto or separated by a linker). Moreover the T cell epitope sequence of the immunogenic peptide and/or the redox motif can be modified and/or one or more flanking sequences and/or a targeting sequence can be introduced (or modified), compared to the naturally occurring T-cell epitope sequence. Accordingly, the resulting sequence of the immunogenic peptide will in most cases differ from the sequence of the intracellular pathogen-associated antigen/protein of interest. In this case, the immunogenic peptides of the invention are peptides with an artificial', non naturally occurring sequence.

The immunogenic peptides of the invention can vary substantially in length, e.g. from about 12-13 amino acids (a T-cell epitope of 8-9 amino acids and the 4-amino acid redox motif) to up to 50 or more amino acids. For example, an immunogenic peptide according to the invention may comprise an endosomal targeting sequence of 40 amino acids, a flanking sequence of about 2 amino acids, a motif as described herein of 4 amino acids, a linker of 4 amino acids and a T cell epitope peptide of 9 amino acids. In particular embodiments, the immunogenic peptides of the invention consist of between 12 amino acids and 20 up to 25, 30, 50, 75, 100 or 200 amino acids. In a more particular embodiment, the peptides consist of between 10 and 20 amino acids. More particularly, where the reducing compound is a redox motif as described herein, the length of the immunogenic peptide comprising the epitope and motif optionally connected by a linker is 19 amino acids or less, e.g., 12, 13, 14, 15, 16, 17, 18 or 19 amino acids.

As detailed above, the immunogenic peptides for use in the targeting of intracellular pathogens according to the invention comprise a reducing motif as described herein linked to a T cell epitope sequence. According to a particular embodiment the T-cell epitopes are derived from intracellular pathogen-associated antigens which do not comprise within their native natural sequence an amino acid sequence with redox properties within a sequence of 11 amino acids N- or C-terminally adjacent to the T-cell epitope of interest. Most particularly, the invention encompasses generating immunogenic peptides from intracellular pathogen-associated antigens which do not comprise a sequence selected from C-X(2)-S(SEQ ID NO: 29), S-X(2)-C(SEQ ID NO: 31), C-X(2)-C (SEQ ID NO: 28), S-X(2)-S(SEQ ID NO: 32), C-X(2)-T (SEQ ID NO: 30), T-X(2)-C (SEQ ID NO: 33) within a sequence of 11 amino acids N- or C-terminally adjacent to the epitope sequence. In further particular embodiments, the present invention provides immunogenic peptides of intracellular pathogen-associated antigens which do not comprise the above-described amino acid sequences with redox properties within their sequence.

In further particular embodiments, the immunogenic peptides of the invention are peptides comprising T cell epitopes which do not comprise an amino acid sequence with redox properties within their natural sequence. However, in alternative embodiments, a T cell epitope binding to the MHC cleft may comprise a redox motif such as described herein within its epitope sequence; the immunogenic peptides according to the invention comprising such T-cell epitope must further comprise another redox motif coupled (adjacent or separated by a linker) N- or C-terminally to the epitope such that the attached motif can ensure the reducing activity (contrary to the motif present in the epitope, which is buried within the cleft).

Another aspect of the present invention relates to methods for generating immunogenic peptides of the present invention described herein. Such methods include the identification of T-cell epitopes in an intracellular pathogen-associated antigen of interest; ways for in vitro and in silico identification T-cell epitopes are amply known in the art and some aspects are elaborated upon hereafter. The generated immunogenic peptides can be assessed for the capability to induce intracellular pathogen-associated antigen-specific CD4+ regulatory T cells which are cytotoxic for cells presenting (parts of) the intracellular pathogen-associated antigen of interest.

Immunogenic peptides according to the invention are generated starting from T cell epitope(s) of the intracellular pathogen-associated antigen(s) of interest. In particular, the T-cell epitope used may be a dominant T-cell epitope. The identification and selection of a T-cell epitope from an intracellular pathogen-associated antigen, for use in the context of the present invention is known to a person skilled in the art. For instance, peptide sequences isolated from an intracellular pathogen-associated antigen are tested by, for example, T cell biology techniques, to determine whether the peptide sequences elicit a T cell response. Those peptide sequences found to elicit a T cell response are defined as having T cell stimulating activity. Human T cell stimulating activity can further be tested by culturing T cells obtained from an individual sensitized to an intracellular pathogen-associated antigen with a peptide/epitope derived from the intracellular pathogen-associated antigen and determining whether proliferation of T cells occurs in response to the peptide/epitope as measured, e.g., by cellular uptake of tritiated thymidine. Stimulation indices for responses by T cells to peptides/epitopes can be calculated as the maximum CPM in response to a peptide/epitope divided by the control CPM. A T cell stimulation index (S.I.) equal to or greater than two times the background level is considered "positive." Positive results are used to calculate the mean stimulation index for each peptide/epitope for the group of peptides/epitopes tested. Non-natural (or modified) T-cell epitopes can further optionally be tested for their binding affinity to MHC class II molecules. The binding of non-natural (or modified) T-cell epitopes to MHC class II molecules can be performed in different ways. For instance, soluble HLA class II molecules are obtained by lysis of cells homozygous for a given class II molecule. The latter is purified by affinity chromatography. Soluble class II molecules are incubated with a biotin-labelled reference peptide produced according to its strong binding affinity for that class II molecule. Peptides to be assessed for class II binding are then incubated at different concentrations and their capacity to displace the reference peptide from its class II binding is calculated by addition of neutravidin. Methods can be found in for instance Texier et al., (2000) *J. Immunology* 164, 3177-3184). The immunogenic peptides of the invention have a mean T cell stimulation index of greater than or equal to 2.0. An immunogenic peptide having a T cell stimulation index of greater than or equal to 2.0 is considered useful as a prophylactic or therapeutic agent. More particularly, immunogenic peptides according to the invention have a mean T cell stimulation index of at least 2.5, at least 3.5, at least 4.0, or even at least 5.0. In addition, such peptides typically have a positivity index (P.I.) of at least about 100, at least 150, at least about 200 or at least about 250. The positivity index for a peptide is determined by multiplying the mean T cell stimulation index by the percent of individuals, in a population of individuals sensitive to an intracellular pathogen-associated antigen (e.g., at least 9 individuals, at least 16 individuals or at least 29 or 30, or even more), who have T cells that respond to the peptide (thus corresponding to the SI multiplied by the promiscuous nature of the peptide/epitope). Thus, the positivity index represents both the strength of a T cell response to a peptide (S.I.) and the frequency of a T cell response to a peptide in a population of individuals sensitive to an intracellular pathogen-associated antigen. In order to determine optimal T cell epitopes by, for example, fine mapping techniques, a peptide having T cell stimulating activity and thus comprising at least one T cell epitope as determined by T cell biology techniques is modified by addition or deletion of amino acid residues at either the N- or C-terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. T cell epitopes or peptides are selected based on various factors, including the strength of the T cell response to the peptide/epitope (e.g., stimulation index) and the frequency of the T cell response to the peptide in a population of individuals.

Candidate antigens can be screened by one or more in vitro algorithms to identify a T cell epitope sequence within an antigenic protein. Suitable algorithms are described for example in Zhang et al. (2005) *Nucleic Acids Res* 33, W180-W183 (PREDBALB); Salomon & Flower (2006) *BMC Bioinformatics* 7, 501 (MHCBN); Schuler et al. (2007) *Methods Mol Biol.* 409, 75-93 (SYFPEITHI); Donnes & Kohlbacher (2006) *Nucleic Acids Res.* 34, W194-W197 (SVMHC); Kolaskar & Tongaonkar (1990) *FEBS Lett.* 276, 172-174 and Guan et al. (2003) *Appl Bioinformatics* 2, 63-66 (MHCPred). More particularly, such algorithms allow the prediction within an antigenic protein of one or more nonapeptide sequences which will fit into the groove of an MHC II molecule.

The immunogenic peptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques. Recombinantly produced immunogenic peptides of the invention can be derived from a larger precursor protein, e.g., via enzymatic cleavage of enzyme cleavage sites inserted adjacent to the N- and/or C-terminus of the immunogenic peptide, followed by suitable purification.

In view of the limited length of the immunogenic peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205. This provides the tremendous potential to achieve protein synthesis which is beyond the scope of SPPS. Many proteins with the size of 100-300 residues have been synthesised successfully by this method. Synthetic peptides have continued to play an ever-increasing crucial role in the research fields of biochemistry, pharmacology, neurobiology, enzymology and molecular biology because of the enormous advances in the SPPS.

The physical and chemical properties of an immunogenic peptide of interest (e.g. solubility, stability) is examined to determine whether the peptide is/would be suitable for use in therapeutic compositions. Typically this is optimised by adjusting the sequence of the peptide. Optionally, the peptide can be modified after synthesis (chemical modifications e.g. adding/deleting functional groups) using techniques known in the art.

In yet a further aspect, the present invention provides methods for generating intracellular pathogen-associated antigen-specific cytotoxic T cells (Tregs or CD4+ regulatory T-cells) either in vivo or in vitro (ex vivo). In particular T cells are provided which are cytotoxic towards any cell presenting an intracellular pathogen-associated antigen and are obtainable as a cell population. The invention extends to (populations of) intracellular pathogen-associated antigen-specific cytotoxic Tregs obtainable by the herein described methods.

In particular embodiments, methods are provided which comprise the isolation of peripheral blood cells, the stimulation of the cell population in vitro by contacting an immunogenic peptide according to the invention with the isolated peripheral blood cells, and the expansion of the stimulated cell population, more particularly in the presence of IL-2. The methods according to the invention have the advantage that higher numbers of Tregs are produced and that the Tregs can be generated which are specific for the intracellular pathogen-associated antigen (by using a peptide comprising an antigen-specific epitope). Alternatively, intracellular pathogen-associated antigen-specific cytotoxic T cells may be obtained by incubation in the presence of APCs presenting an intracellular pathogen-specific immunogenic peptide according to the invention after transduction or transfection of the APCs with a genetic construct capable of driving expression of such immunogenic peptide. Such APCs may in fact themselves be administered to a subject in need to trigger in vivo in said subject the induction of the beneficial subset of cytotoxic CD4+ T-cells which are also capable of stimulating non-specific intracellular microbicidal mechanisms in cells of said subject infected with an intracellular pathogen.

In an alternative embodiment, the Tregs can be generated in vivo, i.e. by the administration of an immunogenic peptide provided herein to a subject, and collection of the Tregs generated in vivo.

The intracellular pathogen-associated antigen-specific regulatory T cells obtainable by the above methods are of particular interest for use in the manufacture of a medicament for preventing or treating infection with an intracellular antigen. For any of the above-described uses of the immunogenic peptides of the invention, said peptides can be replaced by said intracellular pathogen-associated antigen-specific Tregs. Both the use of allogeneic and autogeneic cells is envisaged. Any method comprising the administration of said intracellular pathogen-associated antigen-specific Tregs to a subject in need (i.e., for preventing or treating infection with an intracellular pathogen) is also known as adoptive cell therapy. Tregs are crucial in immunoregulation and have great therapeutic potential. The efficacy of Treg-based immunotherapy depends on the Ag specificity of the regulatory T cells. Moreover, the use of Ag-specific Treg as opposed to polyclonal expanded Treg reduces the total number of Treg necessary for therapy.

A further aspect of the present invention relates to nucleic acid sequences encoding the immunogenic peptides of the present invention and methods for their use, e.g., for recombinant expression or in gene therapy. In particular, said nucleic acid sequences are capable of expressing an immunogenic peptides of the invention.

The immunogenic peptides of the invention may indeed be administered to a subject in need by using any suitable gene therapy method. In any use or method of the invention for the prevention and/or treatment of infection with an intracellular pathogen, immunisation with an immunogenic peptide of the invention may be combined with adoptive cell transfer of (a population of) Tregs specific for said immunogenic peptide and/or with gene therapy. When combined, said immunisation, adoptive cell transfer and gene therapy can be used concurrently, or sequentially in any possible combination.

In gene therapy, recombinant nucleic acid molecules encoding the immunogenic peptides can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognised by the cells normal mechanisms for transcription and translation, and a gene product will be expressed. Other methods have also been described for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilising endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding an immunogenic peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for an immunogenic peptide according to the invention may be used in gene therapy.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the introduced nucleic acid.

According to the present invention medicaments are envisaged i.a. for the treatment of infection with intracellular pathogens. The medicament of the invention is usually, but not necessarily, a (pharmaceutical) formulation comprising as active ingredient at least one of the immunogenic peptides of the invention, a (population of) Tregs specific for said immunogenic peptide or a gene therapeutic vector capable of expressing said immunogenic peptide. Apart from the active ingredient(s), such formulation will comprise at least one of a (pharmaceutically acceptable) diluent, carrier or adjuvant. Typically, pharmaceutically acceptable compounds (such as diluents, carriers and adjuvants) can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated. In particular, the pharmaceutical compositions of the invention are vaccines for prophylactic or therapeutic application.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need in a single administration can also vary and will depend on factors such as the physical status of the subject (e.g., weight, age), the status of the condition to be prevented or treated, and the experience of the treating doctor, physician or nurse.

The term “diluents” refers for instance to physiological saline solutions. The term “adjuvant” usually refers to a pharmacological or immunological agent that modifies (preferably increases) the effect of other agents (e.g., drugs, vaccines) while having few if any direct effects when given by themselves. As one example of an adjuvant aluminium hydroxide (alum) is given, to which an immunogenic peptide of the invention can be adsorbed. Further, many other adjuvants are known in the art and can be used provided they facilitate peptide presentation in MHC-class II presentation and T cell activation. The term “pharmaceutically acceptable carrier” means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Immunogenic peptides, homologues or derivatives thereof according to the invention (and their physiologically acceptable salts or pharmaceutical compositions all included in the term “active ingredients”) may be administered by any route appropriate to the condition to be prevented or treated and appropriate for the compounds, here the immunogenic proteins to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

A further aspect of the invention relates to isolated immunogenic peptides comprising a T-cell epitope from an intracellular pathogen-associated antigen and, adjacent to said T-cell epitope or separated from said T-cell epitope by a linker, a C-(X)2-[CST] (SEQ ID NO: 26) or [CST]-(X)2-C(SEQ ID NO: 27) motif. In particular embodiments the intracellular pathogen associated antigen is an antigen of a virus, more particularly a capsid protein.

The present invention will now be illustrated by means of the following examples, which are provided without any limiting intention. Furthermore, all references described herein are explicitly included herein by reference.

EXAMPLES

Example 1. Cytotoxic Regulatory T Cells to Adenovirus Elicit Increased Generation of Reactive Oxygen Intermediates in Dendritic Cells Presenting the Cognate Peptide Adenovirus of serotype 5 (Ad.RR5, E1/E3-deleted) was used in these experiments. Thus, 5 μL of a solution containing $2\times10^{11}$ viral particles/ml was administered by the intravenous route to 6 weeks old C57Bl/6 mice. Ten days later, the spleen of such mice was recovered and CD4+ T cells purified by magnetic sorting.

A T cell epitope was identified within the sequence of the major capsid protein, by a combination of algorithms. A T cell epitope encompassing amino acid residues 912-921 was selected, with sequence: PTLLYVLFEV (SEQ ID NO:1; natural epitope). A synthetic peptide encoding this natural epitope sequence was obtained. A second peptide additionally containing a thioreductase consensus sequence (or redox motif) was synthesised and has the sequence: CHGCPTLLYVLFEV (SEQ ID NO:2; redox motif underlined; modified epitope).

CD4+ T cells obtained from Ad.RR5-immunized mice were cultured in the presence of T lymphocyte-depleted spleen adherent cells used as antigen-presenting cells pre-incubated with either peptide of SEQ ID NO:1 or peptide of SEQ ID NO:2. After two cycles of restimulation, the CD4+ T cell lines were allowed to rest for 10 days. Cell lines expanded with the peptide of SEQ ID NO:1 were then compared to cell lines expanded with the peptide of SEQ ID NO:2 in an assay in which dendritic cells from naïve C57Bl/6 mice were used for antigen presentation. The generation of reactive oxygen intermediates (ROI) by dendritic cells was then evaluated after 2 h of co-culture. Dendritic cells were prepared from the spleen of C57Bl/6 mice by sorting on magnetic beads coated with an anti-CD11c specific antibody.

Thus, $10^5$ dendritic cells were incubated for 1 h with 10 μM DCFDA, a derivative of fluorescein used as an indicator of ROI generation. In a control experiment, no peptide was used to load the dendritic cells, which were then incubated for 18 h with $2\times10^5$ CD4+ T cell line obtained by expansion with peptide of SEQ ID NO:1 or of SEQ ID NO:2 to establish a background value for the generation of ROI. In parallel experiments $10^5$ dendritic cells were loaded with 10 μM DCFDA during 1 hour together with 10 μg of peptide of SEQ ID NO:1 (natural sequence). These loaded dendritic cells were then co-cultured for 2 h at 37° C. with $2\times10^5$ of a CD4+ T cell line expanded with peptide of either SEQ ID NO:1 or SEQ ID NO:2. The production of ROI by dendritic cells was shown to be induced in antigen-presenting cells using Facs analysis. Fluorescence increases generated by DCFDA oxidation by reactive oxygen intermediates are read in a Facs gated on CD11c(+) cells.

FIG. 1 shows that dendritic cells loaded with peptide of SEQ ID NO:1 produced significantly more ROI when co-cultured with a T cell line expanded with peptide of SEQ ID NO:2. These experiments show that, compared to natural intracellular pathogen-derived T-cell epitopes, such epitopes modified by attachment of a thioreductase motif trigger an increased generation of reactive oxygen intermediates in cells presenting the natural T-cell epitope.

Example 2. *Mycobacterium tuberculosis*

*Mycobacterium tuberculosis* is responsible for thousands of deaths every year. The only available vaccination, the Calmette-Guérin *Mycobacterium bovis*-based vaccine (BCG), is not efficient. In addition, several *mycobacterium* strains show resistance to conventional chemotherapy. Antigen-specific CD4+ cells are known to occur in tuberculosis (Winslow et al. (2003) *J. Immunol.* 170:2046-2052), which can be protective (Khader et al. (2007) *Nature Immunol.* 8:369-377).

The early secretory antigen (ESA) produced by *M. tuberculosis* is one of the main antigens recognised both by humans and animals such as mice. A dominant T cell epitope, called ESAT-6, corresponding to the amino acid sequence 1-20, has been mapped and shown to be promiscuous, as it activates CD4+ T cells in major mouse strains and in humans. A (natural) T-cell epitope has been identified that contains amino acids 3-17, with sequence: FAGIEAAAS (SEQ ID NO:3). Addition of a consensus sequence CGHC (SEQ ID NO: 40) with thioreductase activity (shortly: redox motif) at the amino terminal end of the peptide generates a modified T-cell epitope with sequence: CGHCFAGIEAAAS (SEQ ID NO:4; redox motif underlined).

C57Bl/6 mice are immunised with the peptide of SEQ ID NO:3 together with an adjuvant such as alum. Three injections of 50 μg of the peptide are made at fortnight intervals. Two weeks after the last immunisation, mice are sacrificed and CD4+T lymphocytes prepared from the spleen by a combination of density gradient centrifugation and selection on antibody-coated magnetic beads. CD4+T cells are then activated and expanded in vitro using antigen-presenting cells loaded with peptide of SEQ ID NO:4, and cloned by limiting dilution.

The production of reactive oxygen and reactive nitrogen intermediates is shown to be induced in antigen-presenting cells using Facs analysis and RT-PCR, respectively, as follows. Dendritic cells are prepared from the spleen of C57Bl/6 mice by sorting on magnetic beads coated with an anti-CD11c specific antibody. Dendritic cells are pre-incubated for 1 h with both 10 μM DCFDA, a derivative of fluorescein used as an indicator of reactive oxygen intermediate generation and with 10 μg of peptide of SEQ ID NO:3. Thereafter, $10^5$ dendritic cells are co-cultured with $2\times10^5$ CD4+ T cells for 2 h at 37° C. Fluorescence increase generated by DCFDA oxidation by reactive oxygen intermediates are read in a Facs gated on CD11c(+) cells. The production of reactive nitrogen species is evaluated by increased transcription of induced nitric oxide synthase. Thus, $5\times10^5$ dendritic cells prepared as above from the spleen of C57Bl/6 mice are co-cultured for 6 h with $10^6$ CD4+ T cells and peptide of SEQ ID NO:4. Cells are then treated with 2 mM EDTA in cold phosphate-buffered saline to dissociate CD4+ T cells from dendritic cells. Dendritic cells are then purified using magnetic beads coated with anti-CD11c antibodies and analysed by RT-PCR for the presence of transcripts of nitric oxide synthase.

In addition, dendritic cells and CD4+ T cells prepared as described above are co-cultured for 12 h in the presence of peptide of SEQ ID NO:4. Then 5 μM DAF-FM diacetate (amino-methylamino difluorescein diacetate) is added for 30 minutes followed by washing the cells. Cells are then analyzed by flow cytometry gated on CD11c(+) cells. The presence of reactive nitrogen intermediates increases the fluorescence generated by DAF-FM.

To evaluate the cytolytic properties of CD4+ T cell clones activated by peptide of SEQ ID NO:4, dendritic cells are loaded with peptide of SEQ ID NO:3 and mixed at a 1/1 ratio with CD4+ T cells.

After an incubation period of 18 h, dendritic cells are analysed by flow cytometry for expression of apoptosis markers. Thus, annexin V binding to the surface of apoptotic cells is detected by addition of a fluorescence-labelled annexin V.

Example 3. *Plasmodium falciparum*

*Plasmodium falciparum* is a parasite responsible for malaria. The disease develops after mosquito biting. Infected mosquitoes inject sporozoites from *Plasmodium* into the bloodstream, which are taken by hepatocytes in which they transform into the merozoite form. Upon lysis of hepatocytes merozoites are taken up by erythrocytes, which results in massive hemolysis.

There is no satisfying vaccine available and malaria is responsible for ±1 million deaths a year, despite the use of chemicals to which the parasite often becomes resistant, such as nivaquine.

There are two steps at which vaccination could be envisaged (De Groot et al. (1989) *J. Immunol.* 142:4000-4005; Reece et al. (2004) *Nature Med.* 10:406-410). Prevention could be best obtained if the sporozoite form of the parasite was prevented from invading hepatocytes. Attenuation of ongoing disease could be achieved by targeting the merozoite form to prevent erythrocyte entry. Current efforts in vaccine development are essentially centered on prevention. Thus, a number of antigens of the sporozoite form have been considered for the design of specific vaccination (Good et al. (1988) *J. Immunol.* 140:1645-1650).

The CSP antigen (circumsporozoite protein) is the predominant protein at the surface of the parasite. It is a 120-aminoacid residue-long protein with a molecular mass of 58 kDa.

Two regions containing promiscuous T cell epitopes have been identified in the carboxy-terminal end of the protein. The (natural) Th2R epitope has been mapped to amino acid residues 328-336 and corresponds to DKHIEQYLK (SEQ ID NO:5) which is a promiscuous T cell epitope recognised by several mouse strains including H2d mice and ±50% of human beings. This T-cell epitope is modified by addition of a sequence of 4 amino acids carrying a thioredox consensus motif of the type CGHC (SEQ ID NO: 40), which generates a peptide of sequence: CGHCDKHIEQYLK (SEQ ID NO:6; consensus motif underlined; modified T-cell epitope).

A second (natural) T cell epitope, which offers much less polymorphism yet maintaining promiscuity, encompasses residues 380-388 within the same region of the CSP antigen, the sequence of which is:
EKKICKMEK (SEQ ID NO:7). Addition of a consensus motif of the type CGHC (SEQ ID NO: 40) at the amino-terminal end of this T-cell epitope generates a new peptide of sequence: CGHCEKKICKMEK (SEQ ID NO:8; consensus motif underlined; modified T-cell epitope).

In an experimental setting similar to that described above for *Mycobacterium tuberculosis* (see Example 1), CD4+ T cell clones elicited by immunization of BALB/c with peptide of SEQ ID NO:6 or 8, or both, are analyzed for their capacity to induce apoptosis of antigen-presenting cells presenting natural peptide of SEQ ID NO:5 or 7, or the two together.

Parallel experiments demonstrate that the contact between CD4+ cytolytic T cells and dendritic cells induces a reverse signalling leading to expression of IDO. Thus, $10^6$ dendritic cells pre-loaded with peptide of SEQ ID NO:5 or 7 are co-cultured with $2\times10^6$ CD4+ T cells obtained from the spleen of mice immunised with peptide of SEQ ID NO:6 or 8, respectively. After 8 h incubation, dendritic cells are separated from CD4+ T cells by treatment with cold phosphate buffered saline containing 2 mM EDTA. Dendritic cells are then separated from CD4+ T cells by sorting on magnetic beads coated with an anti-CD11c specific antibody. Dendritic cells are then analysed by Western blotting for the presence of IDO (indolamine-2,3-dioxygenase).

To evaluate the respective roles of IFN-gamma and of CTLA-4 in the induction of IDO, the experiments are carried out in the presence of either 20 μg/ml of anti-IFN-gamma antibody, or in the presence of recombinant soluble CD80 and CD86 (10 μg/ml).

Example 4. Influenza Virus

The influenza virus, like any other virus, is an obligate intracellular pathogen. It is well known to affect people by the millions every year for reasons, which are related to its high degree of contagiousness and capacity to mutate rapidly, rendering acquired immunity inoperant from one year to the other. The virus carries a very significant morbidity and mortality. Current vaccination strategies make use of surface proteins such as hemagglutinin and neuraminidase, which induce high titres of specific antibodies but are rather inefficient at eliciting cytolytic T cells that would eliminate infected cells.

The hemagglutinin antigen carries a number of T cell epitopes that are presented in the context of MHC-class II determinants and activate effector T cells, which provide help for the production of specific antibodies.

Thus the peptide KYVKQNTLK (SEQ ID NO:9) encompasses a (natural) CD4+ T cell epitope recognised by both mouse strains and human beings. This T-cell epitope is modified by addition of a sequence of 4 amino acids carrying a thioredox consensus motif of the type CGHC (SEQ ID NO: 40), which generates a peptide of sequence: CGHCKYVKQNTLK (SEQ ID NO:10; consensus motif underlined; modified T-cell epitope).

Administration of peptide of SEQ ID NO:10 in the form of a vaccine together with an adjuvant such as alum is assessed for its capacity to expand CD4+ T cells that have acquired cytolytic properties for influenza virus-infected cells. The effect of CD4+ T cell clones elicited by mouse immunisation with peptide of the SEQ ID NO:10 on the induction of apoptosis of antigen-presenting cells presenting the naturally-processed peptide corresponding to SEQ ID NO:9 is analysed.

Methods similar to that described above for *Mycobacterium tuberculosis* or *Plasmodium falciparum* (Examples 1-2) are used to analyse the induction of apoptosis of dendritic cells loaded with peptide of SEQ ID NO:9.

Example 5. Leishmaniasis

*Leishmania* infections are frequent and can adopt different forms, from the benign cutaneous form that cures spontaneously to visceral forms such as kala azar. The disease is caused by infected sandflies, which inject the promastigote form under the skin. This is taken by macrophages, in which they multiply into amastigotes, which can spread over the body if efficient immunity does not develop. The immune response includes antibody formation, but these are not protective. Efficient immunity depends on strong cellular responses (Pingel et al. (1999) *J. Exp. Med.* 189:1111-1120; Gumy et al. (2004) *Int. J. Parasitol.* 34:433-444).

Animal experiments have clearly illustrated the dependence of pathogen clearance on cellular response, at least for

*Leishmania major*. Thus, C57Bl/6 mice (H2b) develop a strong Th1 response and are disease resistant, while BALB/c mice (H2d) develop a Th2 response and are disease-susceptible. The LACK (*Leishmania* activated c kinase) antigen of *Leishmania major* is central in driving the immune response. Thus, LACK possesses 2 major T cell epitopes, which seemingly elicit either a cellular Th1 immune response (in the C57Bl/6 strain) or a Th2 response (in the BALB/c strain).

Thus, immunisation of BALB/c mice with a (natural) T-cell epitope encompassing LACK amino acid residues 163-171, i.e. a peptide with sequence EHPIVVSGS (SEQ ID NO:11), results in the clonotypic expansion of CD4+Th2 cells, producing IL-4, IL-13 and IL-5 together with specific antibodies, and no Th1 cellular response. Modifying peptide of SEQ ID NO:11 by addition of a 4 amino acid thioredox consensus sequence of the type CGHC (SEQ ID NO: 40) results in a new peptide of sequence: CGHCEHPIVVSGS (SEQ ID NO:12; consensus sequence underlined; modified T-cell epitope).

Administration of such peptide in the form of a vaccine together with an adjuvant such as alum is assessed for its capacity to expand CD4+ T cells that have acquired cytolytic properties for *Leishmania major*-infected cells. Thus, BALB/c mice are immunised with peptide of SEQ ID NO:12 using a protocol similar to that described above for *Mycobacterium tuberculosis* or *Plasmodium falciparum* (Examples 1-2). The effect of CD4+ T cell clones elicited by mouse immunisation with peptide of the SEQ ID NO:12 on the induction of apoptosis of antigen-presenting cells presenting the naturally-processed peptide corresponding to SEQ ID NO:11 is analysed Example 6. Immunodeficiency Virus Infection by the human immunodeficiency virus (HIV) is followed by rapid activation of CD4+ T cells followed by progressive depletion of such cells. During this active stage, CD4+ T cells overexpress surface activation markers such as MHC class II determinants. Peptides derived from the virus are processed and presented into MHC class II determinants.

The gp120 subunit of the Env protein of HIV contains epitopes which are presented into MHC class II determinants (Harari et al. (2008) J. Exp. Med. 205:63-77). Thus, a (natural) T-cell epitope corresponding to amino acids 437 to 445 of the gp 120 subunit is constructed and has the sequence: RAMYAPPIA (SEQ ID NO:13). Modifying the T-cell epitope of SEQ ID NO:11 by addition of a 4 amino acid thioredox consensus sequence of the type CGHC (SEQ ID NO: 40) results in a new peptide of sequence: CGHCRAMYAPPIA (SEQ ID NO:14; consensus sequence underlined; modified T-cell epitope).

To establish the proof of concept that T cells presenting an antigen by surface MHC class II determinants can be eliminated by cytolytic T cells of the present invention, C57Bl/6 mice are immunised with peptide of SEQ ID NO:14 by 3 injections of 25 μg of CFA/IFA emulsified peptide made in the footpath at fortnight intervals. CD4+ T cells from such mice are then prepared as described above by a combination of density gradient centrifugation and adsorption of magnetic beads. CD4+ T cells are then expanded in culture in the presence of APC, the peptide of SEQ ID NO:14 and IL-2.

In parallel experiments, CD4+ T cells from the spleen of naïve C57Bl/6 mice are prepared and transduced with a lentivirus construct containing the sequence corresponding to a peptide of SEQ ID NO:13 together with a late endosome targeting sequence. Those methods are known in the art (see Janssens et al. (2003) *Human Gene Therapy* 14:263-276). Transduced T cells are then co-cultured with CD4+ T cells obtained from animals immunised with a peptide of SEQ ID NO:14. The effect of CD4+ T cells on the induction of apoptosis of transduced T cells is analysed.

As rodents, and the mouse in particular, are not permissive to HIV, humanised mice are used. Thus, NOD-SCID (non-obese-diabetes, severe combined immunodeficiency) mice are humanised by reconstitution with human hematopoietic stem cells producing all human lymphoid lineages, autologous fetal liver and thymus. Such mice have been described under the name BLT (bone marrow/liver/thymus) humanised mice (Melkus et al. (2006) *Nature Medicine* 12:1316-1322). BLT mice therefore show human MHC-restricted functional T cells and are known to be susceptible to infection with HIV (Sun et al. (2007) *J. Exp. Med.* 204:705-714).

BLT mice are first immunised with peptide of SEQ ID NO:14 by 3 footpath injections of 25 μg of peptide emulsified in CFA/IFA. Intrarectal administration of a single dose of cell-free HIV-1 is known to result in progressive loss of CD4+ T cells. The effect of immunisation with a peptide of SEQ ID NO:14 eight weeks after HIV-1 inoculation on the number of CD4+ T cells in peripheral blood is analysed.

I claim:

1. An isolated immunogenic peptide having a length of between 12 and 50 amino acids, comprising an MHC class II T-cell epitope from a viral intracellular pathogen-associated antigen and, separated from said MHC class II T-cell epitope by a linker of at most 7 amino acids, a C-(X)2-C (SEQ ID NO: 20) motif; wherein the intracellular pathogen-associated antigen does not comprise within its native natural sequence a C-(X)2-[CST] (SEQ ID NO: 26) or [CST]-(X)2-C(SEQ ID NO: 27) motif with redox properties within a sequence of 11 amino acids N- or C-terminally adjacent to the T-cell epitope.

2. The peptide according to claim 1, wherein the linker has a length of at most 4 amino acids.

3. The peptide according to claim 1, wherein the linker has a length of at most 2 amino acids.

4. The peptide according to claim 1, wherein the peptide has a length of between 12 and 30 amino acids.

5. The peptide according to claim 1, wherein X in the motif is His or Pro.

6. The peptide according to claim 1, wherein X is not Cys.

7. The peptide according to claim 1, wherein the virus is an RNA virus.

8. The peptide according to claim 1, wherein the virus is a single stranded virus.

9. The peptide according to claim 1, wherein the virus is selected from the group consisting of Herpesviridae, Flaviviridae and Picornaviridae.

10. A method for obtaining a peptide comprising the steps of:
identifying a MHC class II T-cell epitope in an antigen of a viral intracellular pathogen; and
producing the immunogenic peptide of claim 1 by chemical synthesis or recombinant expression.

11. A method for inducing apoptosis of virus infected cells that express MHC class II determinants in a human subject, comprising the step of administering to said subject an effective amount of the immunogenic peptide of claim 1.

12. The method according to claim 11, wherein said immunogenic peptide further comprises an endosomal targeting sequence.

13. The method according to claim 11, wherein said motif is positioned N-terminally of the MHC class II T-cell epitope.

14. The method according to claim 11, wherein at least one X in said motif is Gly, Ala, Ser or Thr, and/or at least one C is optionally methylated.

15. The method according to claim 11, wherein at least one X in said motif is His or Pro, and/or at least one C is optionally methylated.

16. The method according to claim 11, wherein said immunogenic peptide is produced by chemical synthesis or by recombinant expression.

17. An in vitro method for obtaining a population of viral intracellular pathogen-associated antigen-specific regulatory human T cells with cytotoxic properties, the method comprising the steps of:
providing human peripheral blood cells;
contacting said cells in vitro with an effective amount of the immunogenic peptide of claim 1; and
expanding said cells in the presence of Interleukin 2 (IL-2).

18. A method for obtaining a population of viral intracellular pathogen-associated antigen-specific regulatory human T cells with cytotoxic properties, the method comprising the steps of:
administering an effective amount of the immunogenic peptide of claim 1 to a human subject; and
obtaining said population of viral intracellular pathogen-associated antigen-specific regulatory T cells from a peripheral blood cell population of said subject.

* * * * *